US012601000B2

(12) United States Patent
Staunig et al.

(10) Patent No.: US 12,601,000 B2
(45) **Date of Patent: *Apr. 14, 2026**

(54) METHOD FOR THE HYDROXYLATION OF STEROIDS

(71) Applicants: ANNIKKI GMBH, Raaba-Grambach (AT); PHARMAZELL GMBH, Raubling (DE)

(72) Inventors: Nicole Staunig, Vasoldsberg (AT); Kai Oliver Donsbach, Traunstein (DE)

(73) Assignees: ANNIKKI GMBH, Raaba-Gramach (AT); PHARMAZELL GMBH, Raubling (DE)

( * ) Notice: Subject to any disclaimer, the term of this patent is extended or adjusted under 35 U.S.C. 154(b) by 100 days.

This patent is subject to a terminal disclaimer.

(21) Appl. No.: 17/909,727

(22) PCT Filed: Mar. 5, 2021

(86) PCT No.: PCT/EP2021/055615

§ 371 (c)(1),
(2) Date: Sep. 6, 2022

(87) PCT Pub. No.: WO2021/176066

PCT Pub. Date: Sep. 10, 2021

(65) Prior Publication Data

US 2024/0209410 A1 Jun. 27, 2024

(30) Foreign Application Priority Data

Mar. 6, 2020 (EP) .................................... 20161537

(51) Int. Cl.

| | |
|---|---|
| ***C12P 33/06*** | (2006.01) |
| ***C12N 9/02*** | (2006.01) |
| ***C12N 9/04*** | (2006.01) |

(52) U.S. Cl.

CPC ............ *C12P 33/06* (2013.01); *C12N 9/0006* (2013.01); *C12N 9/0071* (2013.01); *C12Y 101/01* (2013.01); *C12Y 114/14* (2013.01)

(58) Field of Classification Search

None

See application file for complete search history.

(56) References Cited

FOREIGN PATENT DOCUMENTS

| | | | |
|---|---|---|---|
| CN | 102002518 | A | 4/2011 |
| WO | 2018/227940 | A1 | 12/2018 |
| WO | 2020/109776 | A2 | 6/2020 |

OTHER PUBLICATIONS

Deshcherevskaya et al., J. Mol. Catalysis B: Enzymatic 133: S157-S165 (2016).*

Anonymous. "Putative cytochrome P450 hydroxylase, *Streptomyces hygroscopicus* subsp. *hydroscopicus*" Apr. 6, 2016 (Apr. 6, 2016), abstract No. Database accession No. UPI000767864A, Retrieved from: UniParc [online] XP055806370.

Chalbot S et al: "Use of bioconversion for the preparation of [4-14C]-labeled 7alpha- and 7beta-hydroxylated derivatives of dehydroepiandrosterone and epiandrosterone", Steroids, Elsevier Science Publishers, New York, NY, US, Bd. 67, Nr. 13-14, Dec. 1, 2002 (Dec. 1, 2002), Seiten 1121-1127, XP004393956.

Daniela Schmitz et al. "Steroid conversion with CYP106A2—production of pharmaceutically interesting DHEA metabolites" Microbial Cell Factories, vol. 13, No. 1, Jun. 5, 2014 (Jun. 5, 2014), pp. 1-13 DOI: 10.1186/1475-2859-13-81 ISSN: 1475-2859, 81, XP021190649.

Deshcherevska Ya N O et al. "Search and discovery of actinobacteria capable of transforming deoxycholic and cholic acids" Journal of Molecular Catalysis B: Enzymatic, vol. 133, No. Supplement!, Sep. 1, 2016 (Sep. 1, 2016), pp. SI57-SI65 DOI: 10.1016/J.MOLCATB.2016.12.010 ISSN: 1381-1177, XP085265327.

Giorgi Victoria et al: "Bioprospecting of whole-cell biocatalysts for cholesterol biotransformation", World Journal of Microbiology and Biotechnology, Rapid Communications of Oxford, Oxford, GB, Bd. 35, Nr. 1, Jan. 2, 2019 (Jan. 2, 2019) , Seiten 1-12, XP036685624.

Kollerov V Vet al. "Hydroxylation of lithocholic acid by selected actinobacteria and filamentous fungi" Steroids, Elsevier Science Publishers, New York, NY, US, vol. 78, No. 3, Jan. 18, 2013 (Jan. 18, 2013), pp. 370-378 DOI: 10.1016/J.Steroids.2012.12.010 ISSN: 0039-128X, XP028981316.

Kollerov Vyacheslav et al: "Biotransformation of androstenedione and androstadienedione by selected Ascomycota and Zygomycota fungal strains",Phytochemistry, Elsevier, Amsterdam, NL, Bd. 169, 112160, Oct. 7, 2019 (Oct. 7, 2019), Seiten 1-9, XP085929642.

Li et al: "Synthesis of 7alpha-hydroxy-dehydroepiandrosterone and 7beta-hydroxy-dehydroepiandrosterone", Steroids, Elsevier Science Publishers, New York, NY, US, Bd. 70, Nr. 14, Dec. 15, 2005 (Dec. 15, 2005), Seiten 970-973, XP005171435.

Peter Mrak et al. "Discovery of the actinoplanic acid pathway in Streptomyces rapamycinicus reveals a genetically conserved synergism with rapamycin" Journal of Biological Chemistry, US, vol. 293, No. 52, Oct. 16, 2018 (Oct. 16, 2018), pp. 19982-19995 DOI: 10.1074/jbc.RAI 18.005314 ISSN: 0021-9258, XP055730693.

* cited by examiner

*Primary Examiner* — Erin M. Bowers

(74) *Attorney, Agent, or Firm* — Workman Nydegger

(57) ABSTRACT

The present invention relates to a method of preparing a steroid comprising the step of converting a 7-deoxysteroid with a cytochrome P450 enzyme or a functional variant thereof in the presence of at least one redox partner system and a system for regenerating the redox partner system.

18 Claims, No Drawings

Specification includes a Sequence Listing.

METHOD FOR THE HYDROXYLATION OF STEROIDS

INCORPORATION BY REFERENCE OF SEQUENCE LISTING

This application includes a Sequence Listing submitted electronically in ASCII format. The ASCII copy of the Sequence Listing, created on Jul. 2, 2025, is named 16785-325 Seq List.txt and is 23,291 bytes in size. The ASCII copy of the Sequence Listing is expressly incorporated herein by this reference.

TECHNICAL FIELD

The present invention relates to means and methods for the hydroxylation of steroids.

BACKGROUND OF THE INVENTION 3,7,12-Trihydroxylated bile acids, such as, e.g., cholic acid (3α,7α,12α-trihydroxy-5β-cholanic acid) or ursocholic acid (3α,7β,12α-trihydroxy-5β-cholanic acid), are industrially important chemicals, among other things as starting materials for the manufacture of ursodeoxycholic acid (UDCA). Ursodeoxycholic acid is used, among other things, as a medicament for dissolving minor X-ray negative gallstones as well as for treating the liver diseases primary ciliary cirrhosis and primary sclerosing cholangitis.

The industrially most important source of 3,7,12-trihydroxylated bile acids is biliary fluid from gallbladders, which accumulate as slaughterhouse waste in meat production. Besides other animal species, the bile of cattle is often used. There is no industrially relevant total synthesis for 3,7,12-trihydroxylated bile acids. Since the production of bile acids is linked to another product (meat), the response to increased demands can only be very limited. For this reason, it is of great interest to use the raw material bile as efficiently as possible.

Since bile is an aqueous mixture of bile acids, lipids, cholesterol and other substances, the separation of the components during the extraction of bile acids is of particular importance. The bile acids, in turn, also constitute a mixture the components of which differ in the number and position of the hydroxyl groups. In addition to cholic acid, bovine bile also contains a significant proportion of deoxycholic acid, which differs from cholic acid in that the OH group is missing at position 7 (3α,12α-dihydroxy-5β-cholanic acid). Deoxycholic acid has a much lower commercial value than 3,7,12-trihydroxylated bile acids. Therefore, there is an industrial interest in converting deoxycholic acid into a 3,7,12-trihydroxylated bile acid by selectively introducing a hydroxyl group at position 7.

During hydroxylations, an oxygen atom is formally introduced into a (non-activated) C—H bond in an oxidation reaction. In organic chemistry, these are reactions that are very difficult to perform. OH groups are frequently introduced through detours, e.g., by adding water at a C═C double bond. The selective hydroxylation at a specific position of a complex molecule (such as, e.g., a bile acid) is problematic, since several chemically (almost) equivalent C—H bonds are present.

A method for the enzymatic conversion of lithocholic acid to ursodeoxycholic acid using a 7β-hydroxylase is disclosed in WO 2018/227940 A1.

Schmitz et al. (Microbial Cell Factories 13 (1): 1-13 (2014)) describe the production of 7-hydroxyl derivatives of dehydroepiandrosterone (DHEA) or pregnenolone (PREG) by conversion with a cytochrome P450 monooxygenase.

CN 102 002 518 B discloses the conversion of 3-β-cholesterol acetate to 7-β-hydroxyl-3-β-cholesterol acetate by means of a hydroxylase.

In WO 2020/109776 A2, a method for the hydroxylation or dealkylation of various organic compounds, among other things from the steroid pregnenolone, with a cytochrome P450 is disclosed.

It is an object of the present invention to provide means and methods of hydroxylating steroids, such as bile acids and derivatives thereof, which have a hydrogen and no hydroxyl group at position 7, specifically at this point.

SUMMARY OF THE INVENTION

The object according to the invention is achieved by a method of preparing a steroid having the general formula (I)

(I)

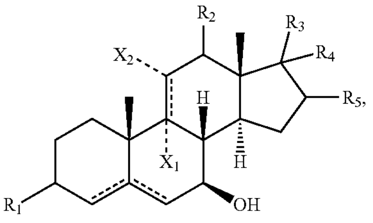

wherein

- $X_1$ and $X_2$ are independently H, Cl, F, Br, I, $CF_3$, a $C_1$ to $C_6$ alkyl radical, OH, a $C_1$ to $C_6$ alkoxy radical, CN, $NO_2$, $N(R_6)_2$, an epoxy group, CHO or a $CO_2R_6$ radical, wherein
  - $R_6$ is $—C(O)H$, $—C(O)CH_3$, $—C(O)CH_2CH_3$, $—C(O)(CH_2)_2CH_3$, $—C(O)CH(CH_3)_2$, $—C(O)(CH_2)_3CH_3$, $—C(O)CH(CH_3)CH_2CH_3$, $—C(O)CH_2CH_2(CH_3)_2$, $—C(O)C(CH_3)_3$, —C(O)Ph, $—C(O)CH_2Ph$,
- $R_1$ and $R_2$ are independently H, OH, OR, or O, wherein
  - $R_7$ is $—C(O)H$, $—C(O)CH_3$, $—C(O)CH_2CH_3$, $—C(O)(CH_2)_2CH_3$, $—C(O)CH(CH_3)_2$, $—C(O)(CH_2)_3CH_3$, $—C(O)CH(CH_3)CH_2CH_3$, $—C(O)CH_2CH_2\ (CH_3)_2$, $—C(O)C(CH_3)_3$, —C(O)Ph, $—C(O)CH_2Ph$,
- $R_3$ is H, OH, ORs, a $C_1$ to $C_{10}$ alkyl radical, a $C_1$ to $C_{10}$ alkenyl radical, —CHO, $—C(O)(CH_3)$, $—C(O)(CH_2OH)$, $—CH(CH_3)C(O)CH_3$, $—CH(CH_3)((CH_2)_2CO_2R_9)$ or $—CH(CH_3)((CH_2)_2CONHR_9)$, wherein
  - $R_8$ is $—C(O)H$, $—C(O)CH_3$, $—C(O)CH_2CH_3$, $—C(O)(CH_2)CH_3$, $—C(O)CH(CH_3)_2$, $—C(O)(CH_2)_3CH_3$, $—C(O)CH(CH_3)CH_2CH_3$, $—C(O)CH_2CH_2\ (CH_3)_2$, $—C(O)C(CH_3)_3$, —C(O)Ph or $—C(O)CH_2Ph$, and
  - $R_9$ is $—CH_3$, $—CH_2COOH$, $—CH_2CH_3$, $—CH(CH_3)_2$, $—(CH_2)_3CH_3$, $—(CH_2)_2SO_3H$, $C(CH_3)_3$, $—(CH_2)_3CH_3$, $—CH(CH_3)CH_2CH_3$, $—CH_2CH_2\ (CH_3)_2$, an aryl group or an alkylaryl group,
- $R_4$ is H, OH, or $—OR_{10}$, wherein
  - $R_{10}$ is $—C(O)H$, $—C(O)CH_3$, $—C(O)CH_2CH_3$, $—C(O)(CH_2)_2CH_3$, $—C(O)CH(CH_3)_2$, $—C(O)(CH_2)_3CH_3$, $—C(O)CH(CH_3)CH_2CH_3$, $—C(O)CH_2CH_2\ (CH_3)_2$, $—C(O)C(CH_3)_3$, —C(O)Ph or $—C(O)CH_2Ph$, and
- $R_5$ is H, $CF_3$, a $C_1$ to $C_6$ alkyl radical, a $C_1$ to $C_6$ alkenyl radical, OH, O, or a $C_1$ to $C_6$ alkoxy radical, wherein the dashed line denotes an optional double bond, with the proviso that the B ring has no double bond if the A ring has a $C_4$-$C_5$ double bond, and the C ring has no double bond if $X_1$ and $X_2$ form an epoxy group, comprising the step of converting a 7-deoxysteroid having the general formula (II)

(II)

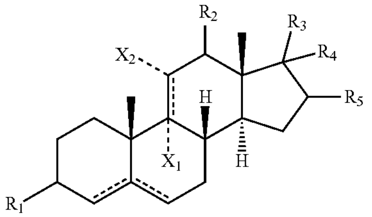

with a cytochrome P450 hydroxylase or a functional variant thereof in the presence of at least one redox partner system and a system for regenerating the redox partner system, the cytochrome P450 enzyme comprising an amino acid sequence which is at least 90%, in particular 100%, identical to the amino acid sequence SEQ ID No. 1 or 2.

Surprisingly, it has been shown that cytochrome P450 and functional fragments thereof are capable of hydroxylating steroids such as cholic acid and, respectively, derivatives thereof having the formula (I) at position 7. By coupling this reaction with at least one redox partner system and a system for regenerating the redox partner system, the equilibrium of the reaction can be shifted towards the end product and the yield thereof can thus be increased significantly. In this case, the regeneration of the redox partner system can take place in the presence of a second system (a regeneration system) which preferably comprises at least one oxidoreductase and at least one substrate of the at least one oxidoreductase.

DESCRIPTION OF THE EMBODIMENTS

Cytochrome P450 and functional variants thereof, which require the oxidation of reducing equivalents NAD(P)H, are surprisingly capable of selectively hydroxylating 7-deoxysteroids, such as, e.g., 7-deoxycholic acid, and derivatives thereof at position 7.

According to the present invention, the cytochrome P450 enzyme comprises an amino acid sequence which is at least 90%, in particular 100%, identical to the amino acid sequence SEQ ID No. 1 or 2.

Cytochromes P450 catalyze monooxygenase reactions of a large number of endogenous as well as exogenous substrates. They are involved, among other things, in the metabolism of steroids, cicosanoids, fatty acids and bile acids as well as of exogenous substrates such as drugs, insecticides and chemical carcinogens.

Cytochromes P450 according to the present invention can be used, for example, from bacteria such as actinobacteria, in particular, for example, from the genus *Streptomyces*. In this case, the sequences can be isolated, for example, from genomic DNA or a cDNA library using known techniques.

The cytochromes P450 according to the present invention and, respectively, their functional variants can optionally be present in their original organism or can be isolated therefrom, or they are expressed recombinantly or produced synthetically. Recombinantly expressed polypeptides are preferably used according to the invention.

Various established microorganisms can be used for the recombinant expression of enzymes according to the present invention, such as, e.g., *Escherichia coli* (*E. coli*), *Bacillus subtilis, Saccharomyces cerevisiae* or *Pichia pastoris*. Appropriate protocols in this regard are described in detail in the relevant specialist literature or are known to a person skilled in the art.

According to the present invention, enzymes/polypeptides are preferably used as proteins recombinantly overexpressed in *E. coli*, with the corresponding cell lysates preferably being used either without further processing/purification or after relatively simple processing steps (e.g., centrifugation, precipitation, concentration or lyophilization). After the recombinant overexpression of the enzymes used, *E. coli* cells can alternatively also be used in the reaction directly without cell disintegration or, for example, after a freezing/thawing cycle. Suitable expression plasmids are known to a person skilled in the art and can often be purchased commercially.

"Functional variants" of cytochrome P450 can be fragments or mutational variants of cytochrome P450, wherein fragments of cytochrome P450 can also be referred to as "functional fragments". "Functional variants" of cytochrome P450 are capable of catalyzing the same reaction as the protein from which they have been derived. Whether a variant is functional, i.e., whether it catalyzes the same reaction as the protein from which it is derived, can be determined by establishing that the variant catalyzes the same reaction. For this purpose, there are established methods in the prior art or, respectively, those that are described herein. The conversion rates of substrates by the functional variants according to the invention can deviate from the conversion rates of the cytochrome P450 from which they have been derived.

"Derivatives of 7-deoxysteroids" comprise compounds derived from 7-deoxysteroids and having a wide variety of modifications as defined above.

According to a preferred embodiment of the present invention, $X_1$, $X_2$, $R_4$ and $R_5$ are H and $R_1$ und $R_2$ are independently H, OH, OR; or O, wherein $R_8$ is —C(O)H, —$C(O)CH_3$, —$C(O)CH_2CH_3$, —C(O)$(CH_2)_2CH_3$, —$C(O)CH(CH_3)_2$, —$C(O)(CH_2)_3CH_3$, —$C(O)CH(CH_3)CH_2CH_3$, —$C(O)CH_2CH_2$ $(CH_3)_2$, —$C(O)C(CH_3)_3$, —C(O)Ph, —$C(O)CH_2Ph$, $R_3$ is a $C_1$ to $C_{10}$ alkyl radical, a $C_1$ to $C_{10}$ alkylen radical, —$CH(CH_3)(CH_2)_2CO_2R_9$) or —$CH(CH_3)((CH_2)_2$ $CONHR_9$), wherein $R_9$ is —$CH_3$, —$CH_2COOH$, —$CH_2CH_3$, —$CH(CH_3)_2$, —$(CH_2)_2CH_3$, —$(CH_2)_2SO_3H$, $C(CH_3)_3$, —$(CH_2)_3$ $CH_3$, —$CH(CH_3)CH_2CH_3$, —$CH_2CH_2$ $(CH_3)_2$, an aryl group or an alkylaryl group.

According to a further preferred embodiment of the present invention, the aryl group is selected from the group consisting of a phenyl radical, a phenyl radical substituted with F, Cl, Br, $NO_2$ or $CH_3$ and a heteroaryl.

According to yet another preferred embodiment of the present invention, the alkylaryl group is selected from the group consisting of a benzyl group, a halogenated benzyl group, wherein the halogen is F, Cl or Br, and a benzyl group substituted with $NO_2$.

According to a preferred embodiment of the present invention, $R_1$ is OH, $R_2$ is O or OH, $R_3$ is $CH(CH_3)((CH_2)_2$ $CO_2R_5$), $R_4$ is H, and $R_5$ is H.

According to another preferred embodiment of the present invention, the 7-deoxysteroid having the general formula (II) is selected from the group consisting of 3α,12α-dihydroxy-5β-cholane-24-acid, 3α,12β-dihydroxy-5β-cholane-24-acid, 3β,12α-dihydroxy-5β-cholane-24-acid, 3β,12β-dihydroxy-5β-cholane-24-acid, 3β-hydroxy-12-keto-5β- cholane-24-acid, 3-keto, 12β-hydroxy-5β-cholane-24-acid, 3-keto, 12α-hydroxy-5β-cholane-24-acid, 3α-hydroxy-5β-cholane-24-acid, 3-keto-5β-cholane-24-acid, 3β-hydroxy-5β-cholane-24-acid and esters of the respective acid.

The cytochrome P450 enzyme used, according to the invention, for the hydroxylation of 7-deoxysteroids and derivatives thereof having the general formula (II) to a steroid or a derivative thereof having the general formula (I) comprises an amino acid sequence which is at least 90%, more preferably at least 95%, more preferably at least 96%, more preferably at least 97%, more preferably at least 98%, more preferably at least 99%, in particular 100%, identical to the amino acid sequence SEQ ID No. 1 or 2.

```
SEQ ID No. 1:
MLTTAETTSIAYPFNTAEGLALSERYEEARNRTGLLRVRMPYGEPAWLVTRYADARLVLGDR

RFSRAEALHHDEPRQSEGRRDSGILTMDPPDHTRLRTLVAKAFTVHQVEKLRPWVRQLTHDL

LDDLEAAGPPADLVDRYALPIPVGVICAMLGVPQEDRPKFRVWSDAALSTSSLSAEQFARNT

DELRAYMAGLIEDHRRIPRDDIMTSLIEARDAGDRLSELELVDLCVGILVAGHETTATQIPN

FVLTLLEHPDQLRRLREDPALIQGAVEELLRFVPLGVGAAQARYATEDIEVGGTLVRSGEPV

LVAVGSANRDALRFDEPGVLNVARPTTQHLGFGHGVHHCLGAPLARLELQEALGALITRFPG

LRLAGDIEWKDRMLVRGPRVMPIGW

SEQ ID No. 2:
MPYGEPAWLVTRYADARLVLGDRRFSRAEALHHDEPRQSEGRRDSGILTMDPPDHTRLRTLV

AKAFTVHQVEKLRPWVRQLTHDLLDDLEAAGPPADLVDRYALPIPVGVICAMLGVPQEDRPK

FRVWSDAALSTSSLSAEQFARNTDELRAYMAGLIEDARRTPRDDIMTSLIEARDAGDRLSEL

ELVDLCVGILVAGHETTATQIFNFVLTLLEHPDQLRRLREDPALIQGAVEELLRFVPLGVGA

AQARYATEDIEVGGTLVRSGEPVLVAVGSANRDALRFDEPGVLNVARPTTQHLGFGHGVHHC

LGAPLARLELQEALGALITRFPGLRLAGDIEWKDRMLVRGPRVMPIGW
```

Amino acid sequences SEQ ID Nos. 1 and 2 are preferably encoded by nucleic acid sequences SEQ ID Nos. 3 and 4, with nucleic acid sequences SEQ ID Nos. 5 and 6 being optimized for expression in *E. coli*.

```
SEQ ID No. 3:
ATGTTGACCACAGCCGAGACGACATCCATCGCCTATCCCTTCAACACCGCCGAAGGGCTGGC

GCTCAGCGAGCGTTACGAAGAGGCCAGGAACCGCACCGGACTGCTCCGGGTGCGGATGCCCT

ACGGTGAGCCCGCCTGGCTGGTCACGCGGTACGCCGACGCCCGGCTGGTGCTCGGCGACCGG

CGCTTCAGCCGTGCGGAGGCGCTCCACCACGACGAGCCGCGGCAGTCCGAAGGCCGGCGCGA

CAGCGGCATCCTGACCATGGACCCGCCCGACCACACCCGGCTGCGCACCCTCGTCGCCAAGG

CGTTCACCGTCCACCAGGTGGAGAAACTCCGCCCCTGGGTACGCCAGTTGACCCATGACCTG

CTCGACGACCTCGAGGCCGCCGGGCCGCCCGCCGATCTGGTGGACCGCTACGCCCTGCCCAT

TCCGGTCGGCGTCATCTGCGCCATGCTCGGCGTCCCGCAGGAGGACCGGCCCAAGTTCCGGG

TCTGGAGCGACGCCGCGCTGTCCACCAGCTCGCTGAGCGCCGAGCAGTTCGCCCGTAACACC

GACGAGCTGCGCGCCTACATGGCCGGGCTGATCGAGGACCACCGCAGGACCCCGCGGGACGA

CATCATGACCTCGCTGATCGAGGCGCGGGACGCGGGCGACCGGCTGTCCGAGCTGGAACTCG

TCGATCTGTGCGTGGGCATCCTGGTGGCCGGGCACGAGACCACCGCCACCCAGATCCCCAAC

TTCGTGCTGACGCTGCTGGAGCACCCGGACCAGCTGCGCCGGCTGCGCGAGGACCCCGCCCT

GATCCAGGGCGCCGTCGAGGAGCTGCTGCGCTTCGTCCCGCTGGGCGTGGGCGCCGCCCAGG

CCCGTTACGCCACCGAGGACATCGAGGTGGGCGGCACGCTGGTGCGCAGCGGGGAGCCGGTG

CTGGTCGCCGTCGGCTCGGCCAACCGCGACGCGCTGCGCTTCGACGAACCGGGCGTGCTCAA

CGTCGCCCGCCCCACCACCCAGCACCTCGGCTTCGGCCACGGTGTGCACCACTGCCTGGGCG

CGCCCCTGGCCCGTCTGGAGCTCCAGGAGGCGCTCGGCGCGCTGATCACGCGCTTCCCGGGC
```

-continued

CTGCGGCTGGCCGGGGACATCGAGTGGAAGGACCGCATGCTGGTCCGCGGGCCCCGTGTCAT

GCCATCGGGTGGTGA

SEQ ID No. 4:
ATGCCCTACGGTGAGCCCGCCTGGCTGGTCACGCGGTACGCCGACGCCCGGCTGGTGCTCGG

CGACCGGCGCTTCAGCCGTGCGGAGGCGCTCCACCACGACGAGCCGCGGCAGTCCGAAGGCC

GGCGCGACAGCGGCATCCTGACCATGGACCCGCCCGACCACACCCGGCTGCGCACCCTCGTC

GCCAAGGCGTTCACCGTCCACCAGGTGGAGAAACTCCGCCCCTGGGTACGCCAGTTGACCCA

TGACCTGCTCGACGACCTCGAGGCCGCCGGGCCGCCCGCCGATCTGGTGGACCGCTACGCCC

TGCCCATTCCGGTCGGCGTCATCTGCGCCATGCTCGGCGTCCCGCAGGAGGACCGGCCCAAG

TTCCGGGTCTGGAGCGACGCCGCGCTGTCCACCAGCTCGCTGAGCGCCGAGCAGTTCGCCCG

TAACACCGACGAGCTGCGCGCCTACATGGCCGGGCTGATCGAGGACCACCGCAGGACCCCGC

GGGACGACATCATGACCTCGCTGATCGAGGCGCGGGACGCGGGCGACCGGCTGTCCGAGCTG

GAACTCGTCGATCTGTGCGTGGGCATCCTGGTGGCCGGGCACGAGACCACCGCCACCCAGAT

CCCCAACTTCGTGCTGACGCTGCTGGAGCACCCGGACCAGCTGCGCCGGCTGCGCGAGGACC

CCGCCTGATCCAGGGCGCCGTCGAGGAGCTGCTGCGCTTCTGTCCCGCTGGGCGTGGGCGCC

GCCCAGGCCCGTTACGCCACCGAGGACATCGAGGTGGGCGGCACGCTGGTGCGCAGCGGGGA

GCCGGTGCTGGTCGCCGTCGGCTCGGCCAACCGCGACGCGCTGCGCTTCGACGAACCGGGCG

TGCTCAACGTCGCCCGCCCCACCACCCAGCACCTCGGCTTCGGCCACGGTGTGCACCACTGC

CTGGGCGCGCCCCTGGCCCGTCTGGAGCTCCAGGAGGCGCTCGGCGCGCTGATCACGCGCTT

CCCGGGCCTGCGGCTGGCCGGGGACATCGAGTGGAAGGACCGCATGCTGGTCCGCGGGCCCC

GTGTCATGCCCATCGGGTGGTGA

SEQ ID No. 5:
ATGCTGACCACCGCAGAAACCACCAGTATTGCATATCCGTTTAATACCGCAGAAGGTCTGGC

ACTGAGCGAACGTTATGAAGAAGCACGTAATCGTACCGGTCTGCTGCGTGTTCGTATGCCGT

ATGGTGAACCGGCATGGCTGGTTACCCGTTATGCAGATGCCCGTCTGGTTCTGGGTGATCGT

CGTTTTAGCCGTGCCGAAGCACTGCATCACGATGAACCGCGTCAGAGCGAAGGTCGTCGTGA

TAGCGGTATTCTGACCATGGATCCGCCTGATCATACCCGTCTGCGTACCCTGGTTGCAAAAG

CATTTACCGTTCATCAGGTTGAAAAACTGCGTCCGTGGGTTCGCCAGCTGACCCATGATCTG

CTGGATGATCTGGAAGCAGCAGGTCCGCCTGCAGATCTGGTTGATCGTTATGCACTGCCGAT

TCCGGTTGGTGTTATTTGTGCAATGCTGGGTGTTCCGCAAGAAGATCGTCCTAAATTTCGTG

TTTGGAGTGATGCAGCACTGAGCACCAGCAGCCTGAGCGCAGAACAGTTTGCACGTAATACC

GATGAACTGCGTGCATATATGGCAGGTCTGATTGAAGATCATCGTCGTACACCGCGTGATGA

TATTATGACCAGCCTGATCGAAGCACGTGATGCCGGTGATCGCCTGAGTGAACTGGAACTGG

TGGATCTGTGTGTTGGTATTCTGGTTGCAGGTCATGAAACCACCGCAACCCAGATTCCGAAT

TTTGTTCTGACCCTGCTGGAACATCCGGATCAGCTGCGTCGTCTGCGTGAAGATCCGGCACT

GATTCAGGGTGCAGTTGAAGAACTGCTGCGTTTTGTTCCGCTGGGTGTGGGTGCAGCACAGG

CACGTTATGCAACCGAAGATATTGAAGTTGGTGGCACCCTGGTTCGTAGTGGCGAACCGGTG

CTGGTTGCCGTTGGTAGCGCAAACCGTGATGCACTGCGCTTTGATGAACCGGGTGTTCTGAA

TGTTGCACGTCCGACCACACAGCATCTGGGTTTTGGTCATGGTGTTCATCATTGTCTGGGTG

CACCGCTGGCACGTCTGGAACTGCAAGAAGCACTGGGAGCACTGATTACCCGTTTTCCGGGT

CTGCGTCTGGCAGGCGATATTGAATGGAAAGATCGTATGCTGGTTCGTGGTCCGCGTGTTAT

-continued

```
GCCGATTGGTTGGTAA

SEQ ID No. 6:
ATGGTGAACCGGCATGGCTGGTTACCCGTTATGCAGATGCCCGTCTGGTTCTGGGTGATCGT

CGTTTTAGCCGTGCCGAAGCACTGCATCACGATGAACCGCGTCAGAGCGAAGGTCGTCGTGA

TAGCGGTATTCTGACCATGGATCCGCCTGATCATACCCGTCTGCGTACCCTGGTTGCAAAAG

CATTTACCGTTCATCAGGTTGAAAAACTGCGTCCGTGGGTTCGCCAGCTGACCCATGATCTG

CTGGATGATCTGGAAGCAGCAGGTCCGCCTGCAGATCTGGTTGATCGTTATGCACTGCCGAT

TCCGGTTGGTGTTATTTGTGCAATGCTGGGTGTTCCGCAAGAAGATCGTCCTAAATTTCGTG

TTTGGAGTGATGCAGCACTGAGCACCAGCAGCCTGAGCGCAGAACAGTTTGCACGTAATACC

GATGAACTGCGTGCATATATGGCAGGTCTGATTGAAGATCATCGTCGTACACCGCGTGATGA

TATTATGACCAGCCTGATCGAAGCACGTGATGCCGGTGATCGCCTGAGTGAACTGGAACTGG

TGGATCTGTGTGTTGGTATTCTGGTTGCAGGTCATGAAACCACCGCAACCCAGATTCCGAAT

TTTGTTCTGACCCTGCTGGAACATCCGGATCAGCTGCGTCGTCTGCGTGAAGATCCGGCACT

GATTCAGGGTGCAGTTGAAGAACTGCTGCGTTTTGTTCCGCTGGGTGTGGGTGCAGCACAGG

CACGTTATGCAACCGAAGATATTGAAGTTGGTGGCACCCTGGTTCGTAGTGGCGAACCGGTG

CTGGTTGCCGTTGGTAGCGCAAACCGTGATGCACTGCGCTTTGATGAACCGGGTGTTCTGAA

TGTTGCACGTCCGACCACACAGCATCTGGGTTTTGGTCATGGTGTTCATCATTGTCTGGGTG

CACCGCTGGCACGTCTGGAACTGCAAGAAGCACTGGGAGCACTGATTACCCGTTTTCCGGGT

CTGCGTCTGGCAGGCGATATTGAATGGAAAGATCGTATGCTGGTTCGTGGTCCGCGTGTTAT

GCCGATTGGTTGGTAA
```

"Identical" as used herein means that two or more amino acid sequences, when superimposed on one another, may have a certain "identity" (matching amino acid residues at identical positions) to one another. "Identity" is defined in this invention as the percentage of amino acids of eligible amino acid sequences that are identical to the amino acids of the starting sequence, namely after the alignment of the two sequences and the introduction of gaps, if necessary, in order to achieve the maximum percentual sequence identity as generated by the "protein BLAST" program (blastp; Altschul et al., J. Mol. Biol. (1997) 215:403-410; http://blast.ncbi.nlm.nih.gov/Blast.cgi; commonly referred to herein as "BLAST"), with all variable parameters set to default values. Herein, the algorithm "blastp (protein-protein-BLAST)" is used with the following parameters: "expect threshold": 0.05; "word size": 6; matrix: BLOSUM62; "gap costs": "Existence" 11, "Extension" 1; conditional compositional score matrix adjustment; no filter and no mask. A percentage (%) value for the amino acid sequence identity is determined by the number of matching identical nucleotides divided by the sequence length for which the identity in percent is recorded.

Using the method according to the invention, 7-deoxysteroids or, respectively, derivatives thereof having the general formula (II) can be converted with cytochrome P450 or a functional variant thereof to steroids or, respectively, derivatives thereof having the general formula (I), with the cytochrome P450 enzyme comprising an amino acid sequence which is at least 90%, in particular 100%, identical to the amino acid sequence SEQ ID No. 1 or 2. This conversion takes place in the presence of redox partners or a redox partner system which is able to provide electrons for the hydroxylation reaction.

According to a preferred embodiment of the present invention, the at least one redox partner system comprises (i) ferredoxin, ferredoxin reductase and NAD(P)H;

(ii) cytochrome P450 reductase and NAD(P)H; or (iii) NAD(P)H.

The redox partner system used according to the invention can comprise ferredoxin, ferredoxin reductase and NAD(P)H; cytochrome P450 reductase and NAD(P)H; or NAD(P)H alone, with a redox partner system comprising ferredoxin, ferredoxin reductase and NAD(P)H being particularly preferred.

In order to carry out the redox reaction of cytochrome P450 according to the invention or, respectively, the functional variants thereof, it is therefore advantageous to use at least the redox cofactors NAD+/NADH and/or NADP+/NADPH in the method according to the invention. In this context, NAD+ designates the oxidized form and NADH designates the reduced form of nicotinamide adenine dinucleotide, whereas NADP+ designates the oxidized form and NADPH designates the reduced form of nicotinamide adenine dinucleotide phosphate.

The concentration of the redox cofactors NAD(P)+ and/or NAD(P)H in a reaction mixture is preferably between 0.001 mM and 10 mM, more preferably between 0.05 mM and 1 mM.

Particularly preferably, ferredoxins are used as redox partners, which can be regenerated in the presence of NAD(P)+ and at least one ferredoxin reductase. According to a preferred embodiment of the present invention, the at least one ferredoxin is selected from the group consisting of adrenodoxins, putidaredoxins and flavodoxins, wherein, optionally, combinations thereof can be used as well.

A possible pair of redox partners preferably comprises putidaredoxin and putidaredoxin reductase from *Pseudomo-*

*nas putida*. Moreover, a person skilled in the art is able to identify further ferredoxin proteins and ferredoxin reductases which are potential redox partners for the cytochrome P450 according to the invention. Suitability as a redox partner can be verified in a functional assay, as described, for example, in Examples 3 to 5. The putidaredoxin used in these examples and/or the putidaredoxin reductase used therein can be replaced by possible alternative proteins or enzymes, respectively. If sufficient formation of the desired product (e.g., ursocholic acid) is observed, the tested redox partners can be regarded as functional alternatives to putidaredoxin and/or putidaredoxin reductase.

According to a particularly preferred embodiment of the present invention, the ferredoxin used in the method according to the invention comprises an amino acid sequence which is at least 80%, preferably at least 85%, more preferably at least 90%, more preferably at least 95%, more preferably at least 96%, more preferably at least 97%, more preferably at least 98%, more preferably at least 99%, in particular 100%, identical to the amino acid sequence SEQ ID No. 7, wherein X is a methionine residue or is not an amino acid.

```
SEQ ID No. 7:
XSKVVYVSHDGTRRELDVADGVSLMQAAVSNGIYDIVGDCGGSASCATC

HVYVNEAFTDKVPAANEREIGMLECVTAELKPNSRLCCQIIMTPELDGI

VVDVPDRQW
```

According to a preferred embodiment of the present invention, the at least one ferredoxin reductase is selected from the group of flavodoxin reductases and putidaredoxin reductase.

The ferredoxin oxidized in the course of the hydroxylation reaction according to the invention can be reduced with the aid of a ferredoxin reductase and NAD(P)H. As a result, reduced ferredoxin is again provided or, respectively, regenerated while consuming NAD(P)H for a further hydroxylation reaction of the substrate according to the invention. The ferredoxin reductase can be a flavodoxin reductase and/or a putidaredoxin reductase.

According to a further preferred embodiment of the present invention, the ferredoxin reductase used in the method according to the invention comprises an amino acid sequence which is at least 80%, preferably at least 85%, more preferably at least 90%, more preferably at least 95%, more preferably at least 96%, more preferably at least 97%, more preferably at least 98%, more preferably at least 99%, in particular 100%, identical to the amino acid sequence SEQ ID No. 8.

```
SEQ ID No. 8:
MNANDNVVIVGTGLAGVEVAFGLRASGWEGNIRLVGDATVIPHHLPPLSKAYLAGKATAE

SLYLRTPDAYAAQNIQLLGGTQVTAINRDRQQVILSDGRALDYDRLVLATGGRPRPLPVA

SGAVGKANNFRYLRTLEDAECIRRQLIADNRLVVIGGGYIGLEVAATAIKANMHVTLLDT

AARVLERVTAPPVSAFYEHLHREAGVDIRTGTQVCGFEMSTDQQKVTAVLCEDGTRLPAD

LVIAGIGLIPNCELASAAGLQVDNGIVINEHMQTSDPLIMAVGDCARFHSQLYDRWVRIE

SVPNALEQARKIAAILCGKVPRDEAAPWFWSDQYEIGLKMVGLSEGYDRIIVRGSLAQPD

FSVFYLQGDRVLAVDTVNRPVEFNQSKQIITDRLPVEPNLLGDESVPLKEIIAAAKAELS

SA
```

Amino acid sequences SEQ ID Nos. 7 and 8 are preferably encoded by nucleic acid sequences SEQ ID Nos. 9 and 10, respectively, with nucleic acid sequences SEQ ID Nos. 11 and 12 being optimized for expression in *E. coli*.

SEQ ID No. 9:
$(ATG)_{0\ or\ 1}$

```
TCTAAAGTAGTGTATGTGTCACATGATGGAACGCGTCGCGAACTGGATGTGGCGGATGGC

GTCAGCCTGATGCAGGCTGCAGTCTCCAATGGTATCTACGATATTGTCGGTGATTGTGGC

GGCAGCGCCAGCTGTGCCACCTGCCATGTCTATGTGAACGAAGCGTTCACGGACAAGGTG

CCCGCCGCCAACGAGCGGGAAATCGGCATGCTGGAGTGCGTCACGGCCGAACTGAAGCCG

AACAGCAGGCTCTGCTGCCAGATCATCATGACGCCCGAGCTGGATGGCATCGTGGTCGAT

GTTCCCGATAGGCAATGGTAA
```

```
SEQ ID No. 10:
ATGAACGCAAACGACAACGTGGTCATCGTCGGTACCGGACTGGCTGGCGTTGAGGTCGCC

TTCGGCCTGCGCGCAAGCGGCTGGGAAGGCAATATCCGGTTGGTGGGGGATGCGACGGTA

ATTCCCCATCACCTACCACCGCTATCCAAAGCTTACTTGGCCGGCAAAGCCACAGCGGAA
```

-continued

ACACAGGTAACGGCTATCAACCGCGACCGACAGCAAGTAATCCTATCGGATGGCCGGGCA

CTGGATTACGACCGGCTGGTATTGGCTACCGGAGGGCGTCCAAGACCCCTACCGGTGGCC

AGTGGCGCAGTTGGAAAGGCGAACAACTTTCGATACCTGCGCACACTCGAGGACGCCGAG

TGCATTCGCCGGCAGCTGATTGCGGATAACCGTCTGGTGGTGATTGGTGGCGGCTACATT

GGCCTTGAAGTGGCTGCCACCGCCATCAAGGCGAACATGCACGTCACCCTGCTTGATACG

GCAGCCCGGGTTCTGGAGCGGGTTACCGCCCCGCCGGTATCGGCCTTTTACGAGCACCTA

CACCGCGAAGCCGGCGTTGACATACGAACCGGCACGCAGGTGTGCGGGTTCGAGATGTCG

ACCGACCAACAGAAGGTTACTGCCGTCCTCTGCGAGGACGGCACAAGGCTGCCAGCGGAT

CTGGTAATCGCCGGGATTGGCCTGATACCAAACTGCGAGTTGGCCAGTGCGGCCGGCCTG

CAGGTTGATAACGGCATCGTGATCAACGAACACATGCAGACCTCTGATCCCTTGATCATG

GCCGTCGGCGACTGTGCCCGATTTCACAGTCAGCTCTATGACCGCTGGGTGCGTATCGAA

TCGGTGCCCAATGCCTTGGAGCAGGCACGAAAGATCGCCGCCATCCTCTGTGGCAAGGTG

CCACGCGATGAGGCGGCGCCCTGGTTCTGGTCCGATCAGTATGAGATCGGATTGAAGATG

GTCGGACTGTCCGAAGGGTACGACCGGATCATTGTCCGCGGCTCTTTGGCGCAACCCGAC

TTCAGCGTTTTCTACCTGCAGGGAGACCGGGTATTGGCGGTCGATACAGTGAACCGTCCA

GTGGAGTTCAACCAGTCAAAACAAATAATCACGGATCGTTTGCCGGTTGAACCAAACCTA

CTCGGTGACGAAAGCGTGCCGTTAAAGGAAATCATCGCCGCCGCCAAAGCTGAACTGAGT

AGTGCCTGA

SEQ ID No. 11:
$(ATG)_{0\ or\ 1}$

ATGAGCAAAGTGGTCTATGTGTCGCATGATGGAACACGCCGTGAGTTAGACGTCGCTGAT

GGTGTATCCCTGATGCAAGCAGCGGTTAGCAATGGCATTTACGACATCGTTGGCGATTGT

GGTGGTAGTGCGTCATGTGCAACGTGTCACGTGTATGTTAACGAAGCGTTTACCGATAAG

GTGCCTGCTGCCAATGAACGCGAGATTGGCATGCTGGAATGCGTAACTGCCGAACTCAAA

CCGAACTCTCGCCTGTGCTGCCAGATCATCATGACCCCGGAATTGGACGGGATTGTCGTT

GATGTGCCAGATCGTCAGTGGTAA

SEQ ID No. 12:
ATGAACGCCAATGATAATGTTGTTATTGTTGGCACCGGTCTGGCAGGCGTTGAAGTTGCA

TTTGGTCTGCGTGCAAGCGGTTGGGAAGGTAATATTCGTCTGGTTGGTGATGCAACCGTT

ATTCCGCATCATCTGCCTCCGCTGAGCAAAGCATATCTGGCAGGTAAAGCAACCGCAGAA

AGCCTGTATCTGCGTACACCGGATGCCTATGCAGCACAGAATATTCAGCTGCTGGGTGGT

ACACAGGTTACCGCAATTAATCGTGATCGTCAGCAGGTTATTCTGAGTGATGGTCGTGCA

CTGGATTATGATCGTCTGGTGCTGGCAACCGGTGGTCGTCCGCGTCCGCTGCCGGTTGCA

AGTGGTGCAGTTGGTAAAGCCAATAACTTTCGTTATCTGCGCACCCTGGAAGATGCAGAA

TGTATTCGTCGTCAGCTGATTGCAGATAATCGCCTGGTTGTGATTGGTGGTGGTTATATT

GGTCTGGAAGTTGCAGCAACCGCCATTAAAGCAAATATGCATGTTACCCTGCTGGATACC

GCACCACGTGTTCTGGAACGTGTTACCGCACCGCCTGTTAGCGCCTTTTATGAACATCTG

CATCGTGAAGCCGGTGTTGATATTCGTACCGGCACCCAGGTTTGTGGTTTTGAAATGAGC

ACCGATCAGCAGAAAGTTACCGCAGTTCTGTGTGAAGATGGCACCCGTCTGCCTGCAGAT

CTGGTTATTGCAGGTATTGGCCTGATTCCGAATTGTGAACTGGCAAGCGCAGCAGGTCTG

CAGGTTGATAATGGTATTGTTATTAACGAACACATGCAGACCAGCGATCCGCTGATTATG

GCAGTTGGTGATTGTGCACGTTTTCATAGCCAGCTGTATGATCGTTGGGTTCGTATTGAA

-continued

```
AGCGTTCCGAATGCACTGGAACAGGCACGTAAAATTGCAGCAATTCTGTGTGGTAAAGTT

CCGCGTGATGAAGCAGCACCGTGGTTTTGGAGCGATCAGTATGAAATTGGTCTGAAAATG

GTTGGTCTGAGCGAAGGTTATGATCGCATTATTGTTCGTGGTAGCCTGGCACAGCCGGAT

TTTTCAGTTTTTTATCTGCAGGGTGATCGTGTGCTGGCAGTTGATACCGTTAATCGTCCG

GTTGAATTTAACCAGAGCAAACAAATTATCACCGATCGTCTGCCGGTGGAACCGAATCTG

CTGGGAGATGAAAGCGTGCCGCTGAAAGAAATTATTGCAGCAGCAAAAGCAGAACTGAGC

AGCGCATA
```

The expression of the cytochrome P450 according to the invention and any ferredoxins and ferredoxin reductases in bacteria, in particular in *E. coli*, is particularly advantageous when nucleic acids with the nucleic acid sequences SEQ ID No. 5, SEQ ID No. 6, SEQ ID No. 11 and/or SEQ ID No. 12 are used. Further aspects of the present invention therefore relate to a nucleic acid (DNA and/or RNA) with a nucleic acid sequence selected from the group consisting of SEQ ID No. 5, SEQ ID No. 6, SEQ ID No. 11 and SEQ ID No. 12 and vectors and/or cells, in particular *E. coli* cells, comprising at least one of those sequences.

It has been shown that it is advantageous if the above-mentioned ferredoxins and ferredoxin reductases are expressed (co-expressed) together with cytochrome P450 in a production strain (e.g., an *E. coli* strain). The ferredoxins, ferredoxin reductases and the cytochrome P450 can also be expressed separately from one another. It is also advantageous to co-express ferredoxin and cytochrome P450 or ferredoxin reductase and cytochrome P450. Through the co-expression of the three proteins or, respectively, enzymes, ideally under the same promoter, an ideal balance between the enzymes can be established, which has a particularly advantageous effect on the enzymatic conversion of a substrate.

According to a preferred embodiment of the present invention, the at least one oxidoreductase is selected from the group consisting of oxidoreductase (EC: 1.1.1), aldehyde dehydrogenase (EC: 1.2.1), amino acid dehydrogenase (EC: 1.4.1), flavin reductase (EC: 1.5.1), transhydrogenase (EC: 1.6.1), nitrite reductase (EC: 1.7.1) and phosphonate dehydrogenase (EC: 1.20.1), preferably selected from the group consisting of alcohol dehydrogenase, hydroxysteroid dehydrogenase, phosphite dehydrogenase and sugar dehydrogenase.

In order to regenerate the redox partner system used in the method according to the invention, in particular the cofactor used in the process (NADH/$NAD^+$ and/or NADPH/$NADP^+$), during the conversion of the steroid having the general formula (I) to a 7-deoxysteroid having the general formula (II), so that the conversion reaction is pushed towards the product, it is advantageous to add a system for regenerating the redox partner system, advantageously oxidoreductases, to the reaction mixture. Oxidoreductases convert substrates by reduction and oxidation, wherein, in the course of those reactions, NADH is oxidized to $NAD^+$ and NADPH is oxidized to $NADP^+$ or, respectively, NAD+ is reduced to NADH and $NADP^+$ is reduced to NADPH. Therefore, the system for regenerating the redox partner system preferably comprises at least one oxidoreductase and at least one substrate of the at least one oxidoreductase.

The oxidoreductase used in the method according to the invention is preferably an alcohol and/or sugar dehydrogenase.

According to a further preferred embodiment of the present invention, the oxidoreductase is selected from the group consisting of glucose dehydrogenase, glucose-6-phosphate dehydrogenase, arabinose dehydrogenase, xylose dehydrogenase, sorbitol dehydrogenase, xylitol dehydrogenase, 12α-hydroxysteroid dehydrogenase, 7α-hydroxysteroid dehydrogenase, 20α-hydroxysteroid dehydrogenase, 17β-hydroxysteroid dehydrogenase, 17α-hydroxysteroid dehydrogenase, 3α-hydroxysteroid dehydrogenase, 3β-hydroxy-delta5 dehydrogenase, 11β-hydroxysteroid dehydrogenase and formate dehydrogenase.

The use of one or several of the above-mentioned oxidoreductases is particularly advantageous for recycling the cofactors used in the conversion reaction.

It has been shown that it is particularly advantageous to add arabinose dehydrogenase, sorbitol dehydrogenase and/or xylitol dehydrogenase to the reaction mixture in order to achieve a high conversion of the substrate into the product.

The reaction mixture can comprise at least one oxidoreductase and one hydroxylase. It is particularly advantageous to add a combination of two or three or more oxidoreductases to the reaction mixture, with a combination of a 12α-hydroxysteroid dehydrogenase and a 7α-hydroxysteroid dehydrogenase or, respectively, a 12α-hydroxysteroid dehydrogenase, a 7α-hydroxysteroid dehydrogenase and an NAD(P)H oxidase or, respectively, an NADH-dependent alcohol dehydrogenase and a hydroxylase or, respectively, an NADPH-dependent alcohol dehydrogenase and a hydroxylase being particularly well suited for the substrate mixtures, for example, for the simultaneous oxidation and hydroxylation of naturally occurring mixtures of cholic acids.

For catalyzing the oxidation or, respectively, reduction reactions of the cofactors in the reaction mixture of the method according to the invention, it is necessary to provide at least one substrate for the oxidoreductases present therein. Therefore, the reaction mixture comprises at least one substrate of the at least one oxidoreductase selected from the group consisting of arabinose, xylose, glucose, sorbitol, xylitol, cholane-24-acid, 3α,12α-dihydroxycholane-24-acid-2,3-butanediol, acetoin, 2-propanol, glutamates, ethanol, phosphonates, phosphites, nitrites, 4-methyl-2-pentanol, 2-butanol, 2-octanol, cyclohexanol, ethanediol, 1,2-propanediol, 1-propanol, 1-butanol, 3-hydroxybutanoate and formate. According to a preferred embodiment of the present invention, the method according to the invention is performed at a temperature of from 10° C. to 40° C., preferably from 15° C. to 38° C., more preferably from 20° C. to 30° C., more preferably from 22° C. to 26° C. It has been shown according to the invention that the enzyme activity of cytochrome P450 for the reaction according to the invention is particularly high in this area.

According to a further preferred embodiment of the present invention, the method according to the invention is performed at a pH of from 6.5 to 8.5, preferably from 7 to 8, more preferably from 7.2 to 7.8. At this pH value, the enzyme activity of cytochrome P450 is highest so as to allow an appropriate conversion of the substrate.

The hydroxylation of deoxysteroids or, respectively, deoxysteroid derivatives can be carried out regioselectively at position 7 of the steroid backbone. In this way, in particular, a 7beta-hydroxyl group can be introduced stereoselectively so that, for example, ursocholic acid and/or ursocholic acid derivatives can be produced.

In a preferred embodiment, the method according to the invention is performed in the presence of at least one organic solvent. Preferably, a single organic solvent is used so that a single-phase system is provided. It is also possible to use a mixture of two or more organic solvents which, according to the invention, are miscible with each other so that a single-phase system is provided. The organic solvent can be protic or aprotic, with aprotic solvents being preferred.

Surprisingly, it has been found that the presence of an organic solvent, in particular an aprotic organic solvent, can significantly increase the conversion of the 7-deoxysteroid of general formula (II) to the steroid of general formula (I) according to the method according to the invention. In addition, the implementation of the method according to the invention in the presence of the organic solvent surprisingly allows the redox partner system to be regenerated.

Alcohols, ethers, esters, glycols, ketones, amides, sulfoxides, organic acids, cycloalkanes, aromatics and chlorinated hydrocarbons can, for example, be used as organic solvents. Examples of suitable organic solvents are methanol, ethanol, isopropanol, 2-butanol, 4-methyl-2-pentanol (methyl isobutyl alcohol, MIBA), diethyl ether ($Et_2O$), diisopropyl ether ($iPr_2O$), dioxane, tetrahydrofuran (THF), 2-methyltetrahydrofuran (Me-THF), ethyl acetate, ethylene glycol, methyl isobutyl ketone (MIBK), 2-butanone, acetone, dimethyl sulfoxide (DMSO), dimethylformamide (DMF), dimethylacetamide (DMA), cyclohexane, toluene, trichloromethane ($CHCl_3$), dichloromethane ($CH_2Cl_2$), hexane or mixtures thereof. Suitable mixtures are, for example, mixtures of hexane and ethyl acetate or isopropanol, as well as mixtures of trichloromethane and phenol. The present invention is not limited to the above exemplary list of solvents.

The organic solvent is preferably an aprotic organic solvent, particularly preferably a solvent selected from the group consisting of dimethylformamide (DMF), dimethyl sulfoxide (DMSO) and dimethylacetamide (DMA).

According to the invention, the amount of the organic solvent is chosen such that the compound of general formula (II) is completely dissolved and the enzyme activity is preserved. Preferably, the compound of formula (II), e.g., lithocholic acid, is dissolved in the organic solvent up to the limit of solubility. In a preferred embodiment, the substrate of the enzyme is placed in the organic solvent.

In the method according to the present invention, the isolation of the product can be effected in different ways. For example, the product can be extracted from the reaction mixture by a suitable organic solvent. Depending on the substrate, such solvents are described in the literature. According to the present invention, cholic acids and their derivatives can be isolated from reaction mixtures, for example, with ethyl acetate, optionally after acidification of the reaction mixture, e.g., with HCl. A method in which bile acids are present in the form of a salt, e.g., a sodium salt, in an aqueous solution constitutes a special case.

In this case, a precipitation of the product can be effected by acidifying the reaction mixture. For this purpose, for example, HCl or dilute HCl can be added to the reaction mixture in a sufficient amount. If a pH value of, for example, 1 to 4, preferably 2 to 3, is achieved in the process, the product predominantly exists in the form of a suspension. The product can then be removed from the reaction mixture by common methods such as, e.g., filtration or centrifugation. Chromatographic methods, such as, e.g., affinity chromatography or ion-exchange chromatography, are another alternative that can be used for product isolation, for example. Furthermore, it is possible, for example, to obtain product by evaporating the reaction solvent.

Alternatively, in a method according to the present invention, the product(s) may also remain in the reaction mixture after the reaction, e.g., in order to carry out even more reactions and optionally isolate an end product upon completion of those reactions. It is also conceivable that the substrate(s) for the method according to the present invention is/are produced in the same reaction batch by previous reactions or reactions taking place in parallel.

A further aspect of the present invention relates to a nucleic acid construct comprising a nucleic acid molecule coding for a cytochrome P450 enzyme as defined above to which 3' end and/or 5' end at least one nucleic acid molecule coding for a polypeptide selected from the group consisting of a ferredoxin, a ferredoxin reductase and an oxidoreductase is bound directly or via a spacer.

The nucleic acid constructs according to the invention are particularly suitable for the production of a steroid as initially defined. By expressing the cytochrome P450 enzyme and at least one protein selected from the group consisting of ferredoxins, ferredoxin reductases and oxidoreductases, starting from a nucleic acid construct, it becomes possible to produce these enzymes or, respectively, proteins in an amount which is necessary for an efficient implementation of the method according to the invention. It is particularly advantageous if all of these proteins are expressed under the control of the same promoter on the nucleic acid construct according to the invention. A further aspect of the present invention is a vector comprising a nucleic acid construct according to the present invention.

The nucleic acid molecule coding for a cytochrome P450 enzyme can be bound to further nucleic acid molecules coding for enzymes or, respectively, proteins, which can be used in the method according to the invention, either directly or via a spacer or, respectively, a spacer sequence. The advantage of such a construct is that such a construct allows to express the enzymes and proteins used in the method according to the invention, in particular cytochrome P450 and ferredoxin and/or ferredoxin reductase, in a comparable amount.

A "spacer" or, respectively, a "spacer sequence" as used herein is a nucleic acid sequence which has neither a stop codon nor any other functional motif. A spacer or, respectively, a spacer sequence serves as a distance holder between two ORFs in order to improve the transcription of these ORFs, if necessary.

According to a preferred embodiment of the present invention, the cytochrome P450 enzyme is encoded by a nucleic acid which is at least 90%, in particular 100%, identical to the nucleic acid sequence SEQ ID No. 3, SEQ ID No. 4, SEQ ID No. 5 or SEQ ID No. 6.

According to a further preferred embodiment of the present invention, the ferredoxin comprises the amino acid sequence SEQ ID No. 7.

According to a particularly preferred embodiment of the present invention, the ferredoxin reductase is an adrenodoxin reductase, preferably a putidaredoxin reductase.

The ferredoxin reductase preferably comprises the amino acid sequence SEQ ID No. 8.

Another aspect of the present invention relates to a vector comprising a nucleic acid construct according to the present invention.

The vector according to the invention can be a cloning or expression vector and, depending on the organism into which it is introduced, can have appropriate sections in order to enable, for example, the transcription of an ORF.

Yet another aspect of the present invention relates to a host cell comprising a nucleic acid construct according to the present invention.

The host cell according to the invention can be used for cloning or for expressing the ORFs that have been introduced recombinantly and are located on a nucleic acid construct.

The lysate of such a host cell can be used in the method according to the invention, provided that the host cell has intracellularly or extracellularly expressed at least one of the enzymes or, respectively, proteins required in the method according to the invention. The 7-deoxy steroid or a derivative thereof having the general formula (II) is thereby preferably brought into contact with a cell suspension or cells in a culture supernatant and/or a lysate of a host cell according to the present invention. Thus, according to a preferred embodiment of the present invention, 7-deoxy steroid or a derivative thereof having the general formula (II) is brought into contact with at least one culture supernatant and/or a lysate of at least one host cell capable of expressing at least one ferredoxin, at least one ferredoxin reductase and/or at least one oxidoreductase.

EXAMPLES

The present invention is explained in further detail using the following examples, without, however, being restricted thereto.

Example 1: Test of Bacterial Strains

The following bacterial strains were obtained from the German Strain Collection of Microorganisms and Cell Cultures (DSMZ [Deutsche Stammsammlung für Mikroorganismen und Zellkulturen]): *Saccharothrix longispora* (DSM-43749), *Catellatospora citrae* (DSM-44097), *Streptomyces hygroscopicus* subsp. *hygroscopicus* (DSM-40578) and *Asanoa ferruginea* (DSM-44099). The strains were cultivated under standard conditions as recommended by DSMZ. As soon as the growth of the cultures had led to visible turbidity, deoxycholic acid (0.5 mM) was added, and it was cultured further for up to 72 h. After a centrifugation step, supernatants of the cultures were extracted with ethyl acetate and analyzed by HPLC and GC/MS. In the HPLC chromatogram of the reaction with *Streptomyces hygroscopicus*, a peak was noted the retention time of which corresponds to that of ursocholic acid. The GC/MS analysis indicated that the potential ursocholic acid peak originates from a bile acid with 3 hydroxyl groups. The examination of the other strains gave no indication of 7-hydroxylated products of deoxycholic acid.

Example 2: Genome Sequencing and Annotation of the P450 Genes

Upon cultivation of *Streptomyces hygroscopicus* subsp. *hygroscopicus* (DSM-40578) according to the DSMZ regulation, the genomic DNA of the strain was isolated (Kieser et al. (2000), Practical *Streptomyces* genetics (Norwich: John Innes Foundation)). The genome was sequenced using Illumina MiSeq, and an assembly based on the known genome of *Streptomyces rapamycinicus* was conducted (Microsynth GmbH, Switzerland). 42 P450 genes could be identified by homology comparisons.

Example 3: Cloning of Expression System

Using the restriction enzyme XhoI, the following construct comprising coding regions for putidaredoxin reductase (PtR) and putidaredoxin (Ptx) was cloned into plasmid pJ411 (DNA 2.0).

Synthetic DNA (Life Technologies): 5', XhoI interface, HindIII interface, approx. 50 bp spacer DNA, ribosome binding site (rbs), ORF (open reading frame) putidaredoxin reductase (PtR), approx. 50 bp spacer DNA, rbs, ORF putidaredoxin (Ptx), XhoI interface, 3'.

The result of the cloning step was checked by means of restriction enzyme digestion and DNA sequencing.

Subsequently, using the restriction enzymes NdeI and HindIII, one ORF each coding for the P450 enzymes identified in Example 2 was cloned into the above-mentioned synthetic DNA or plasmid, respectively (Life Technologies). The result was again verified by means of restriction enzyme digestion and DNA sequencing. The expression vector used in this example and the redox partners used constitute only one way of expressing the cytochrome P450 enzymes according to the invention, which way has been chosen as an example.

The expression plasmids produced with the identified P450 candidates (see example 2) can be used for jointly expressing the respective P450 proteins together with putidaredoxin reductase and putidaredoxin. The 3 ORFs of the respective expression plasmids are expressed under the control of a T7 promoter on a common mRNA, but as separate polypeptides.

Example 4: Expression of P450/Ptx/PtR

After the genome sequencing of *Streptomyces hygroscopicus* subsp. *hygroscopicus*, there were 42 P450 sequences that came into consideration as candidates for a possible deoxycholic acid-7-hydroxylase. To identify the enzyme looked for, ORFs of the candidates were cloned into the expression system described in example 3 and into a pJ411 (DNA 2.0) expression vector without coding regions for putidaredoxin reductase (PtR) and putidaredoxin (Ptx). The following protocol was used for the expression.

TB-P450 expression medium:
- Terrific broth (TB) medium
- +50 μg/ml kanamycin
- +0.5 mM 5-aminolevulinic acid (from 100× parent solution)
- +1 mM thiamine (from 100× parent solution)
- +1 mM $MgCl_2$+2.5 mM ammonium sulfate+50 μM $FeCl_3$ (from 100× parent solution)
- +0.5 mM IPTG (from 1 M parent solution)
- (the additives were each 0.2 μm sterile filtered)

P450 lysis buffer:
- 100 mM Tris pH 7.5
- 20% (v/v) glycerin
- 1 mg/ml lysozyme

The constructs of the P450 candidates, which were to be tested, were transformed into the *E. coli* expression strain BL21 (DE3). Overnight cultures were inoculated from single colonies (LB (lysogeny broth)+kanamycin). The next day, 1:100 expression cultures were inoculated therewith (150 ml TB (terrific broth)—P450 expression medium) and were initially shaken at 37° C. in baffled flasks (1 L) for 3 h. Subsequently, the temperature was lowered to 24° C., and it was shaken for another 22 h. The cultures were harvested by centrifugation at 5000 g for 10 min, washed 1× with 0.9% (w/v) NaCl, and pellets were frozen at −80° C. The cell pellets were thawed, weighed and resuspended with an equivalent amount of P450 lysis buffer, incubated on ice for 1 h and then digested using a sonifier. Upon centrifugation (30 min, 21000 g), the supernatants were used for test reactions.

Example 5: Testing of P450 Candidates for DA Hydroxylation

Reaction mixture:

- 10-80 μl 100 mM NADH (redox cofactor)
- 250 μl 1 M Tris-HCl pH 7.5
- 17.5 μl glycerin (50%)
- 100 μl 50 mM deoxycholic acid solution pH 8.5 (final 10 mM)
- 50 μl *E. coli* lysate P450/PtR/Ptx (see Example 4)
- 17.5-87.5 μl $dH_2O$ The reactions were set up in 1.5 ml screw-top bottles and sealed with lids with aluminium foil. The foil was punctured in several places. It was gently shaken at 24° C. for 18 h. 200 μl of the reaction batch was diluted with 600 μl acetonitrile/5 μl $H_3PO_4$ (50%) and incubated at 55° C. for 15 minutes. Subsequently, the samples were centrifuged at 20817 rcf for 5 minutes and analyzed using HPLC/DAD (e.g., Agilent 1200 series;

column: Merck Purospher STAR RP-18e 125×4 mm, 5 μm;

flow rate: 1.5 ml/min, gradient $H_2O+H_3PO_4$ (pH=2.6)/acetonitrile). One of the examined candidates ("P450_c866") was able to hydroxylate deoxycholic acid to ursocholic acid. The deoxycholic acid used was converted in the process (see the following table). The identity of the product ursocholic acid was verified by GC/MS analysis and by 2D NMR.

| Redox cofactor [μl] | ursocholic acid [μg/ml] | conversion [%] |
|---|---|---|
| 10 | 30 | 3.4 |
| 30 | 48 | 5.3 |
| 50 | 57 | 6.2 |
| 80 | 110 | 11.6 |

In this example, a redox cofactor (NADH) is oxidized by the P450/Ptx/PtR reaction.

Example 6: Testing of P450 Candidates for DA Hydroxylation with Cofactor Recycling of Arabinose Dehydrogenase Reaction mixture:

- 65 μl 100 mM NADH (final 0.5 mM)
- 1 ml 1 M Tris-HCl pH 7.5+20% (v/v) glycerin
- 130 μl 50 mM deoxycholic acid solution pH 8.5 (final 0.5 mM)
- 6.5 μl chloramphenicol solution (final 20 μg/ml)
- 100 μl L-arabinose dehydrogenase
- (from *Burkholderia vietnamiensis*, recombinantly expressed in *E. coli,* 400 U/ml)
- 98 mg L-arabinose (final 50 mM)
- 2.0 ml *E. coli* lysate P450/PtR/Ptx (see example 4)
- 9.6 ml $dH_2O$ The reactions were set up in 50 ml unbaffled Erlenmeyer flasks and sealed with aluminium foil. The film was punctured in several places. It was gently shaken at 24° C. for 16 h. The substances present in the supernatant were extracted with ethyl acetate and evaporated. It was dissolved in a smaller volume of HPLC eluent (methanol/acetonitrile/$H_2O+H_3PO_4$ (pH=3.0); 40:30:33). Subsequently, the samples were analyzed using HPLC/RID (e.g., Agilent 1200 series;

column: Agilent ZORBAX Eclipse XDB-C18 4.6×150 mm, 5 μm; flow rate: 0.8 ml/min). One of the candidates examined ("P450_c866") was able to hydroxylate deoxycholic acid to ursocholic acid. The deoxycholic acid used was almost completely converted in the process (>95%). The identity of the product ursocholic acid was verified by GC/MS analysis and by 2D NMR (data not shown).

In this example, a redox cofactor (NADH) is oxidized by the P450/Ptx/PtR reaction. The redox cofactor is reduced back to its original state by the cofactor regeneration (in this case, for example, using the sugar dehydrogenase arabinose dehydrogenase)(with arabinose being oxidized to arabinolactone/arabonic acid in this case). This enables the use of a substoichiometric amount of redox cofactor.

Example 7: Examples: Conversion Dependent on Cofactor Concentration Conversion with Cofactor Recycling Reaction mixture:

- 10 μl 10 mM NAD+
- 250 μl 100 mM TEA pH 8.2
- 25 μl glycerin (50%)
- 100 μl 50 mM deoxycholic acid solution pH 8.0 (final 10 mM)
- 6.75 mg cells (wW) as a 22.5% suspension in 100 mM TEA pH 8.0 and 25% glycerin
- 5 μl catalase (bovine, Sigma 4 mg/ml)
- 1.7 units xylitol/sorbitol dehydrogenase
- 25 μl 2M sorbitol (final 100 mM)
- 70.8 μl $dH_2O$ The reactions were set up in 1.5 ml screw-top bottles and sealed with lids with aluminium foil. The foil was punctured in several places. It was gently shaken at 24° C. for 18 h.

The recovery of NADH was effected by sorbitol or, respectively, xylitol dehydrogenase in the presence of sorbitol and $NAD^+$.

200 μl of the reaction batch was diluted with 600 μl acetonitrile/5 μl $H_3PO_4$ (50%) and incubated at 55° C. for 15 minutes. Subsequently, the samples were centrifuged at 20817 rcf for 5 minutes and analyzed using HPLC/DAD (e.g., Agilent 1200 series; column: Merck Purospher STAR RP-18e 125×4 mm or Agilent Zorbax XDB-$C_8$ mm 150×4.6 mm, 3.5 μm, 5 μm, flow rate: 1.5 ml/min, gradient $H_2O+H_3PO_4$ (pH=2.6)/acetonitrile).

The deoxycholic acid used was converted quantitatively (100% conversion) to ursocholic acid under the above-mentioned conditions. The identity of the product ursocholic acid was verified by GC/MS analysis and by 2D NMR.

In this example, a redox cofactor (NADH) obtained by the cofactor recycling system sorbitol/xylitol dehydrogenase/sorbitol/$NAD^+$ is used for the hydroxylation reaction. However, other systems for cofactor recycling can also be used (see the following table).

| Regeneration enzyme/ oxidoreductase | μl lysate oxidoreductase | redox cofactor | concentration [mM] | substrate oxidoreductase | concentration [mM] | DOCA conversion [%] |
|---|---|---|---|---|---|---|
| xylitol/sorbitol dehydrogenase | 1.7 | NAD+ | 0.2 | sorbitol | 100 | 100% |
| arabinose dehydrogenase | 3 | NADH | 0.5 | arabinose | 50 | 95% |
| 12α-hydroxy-steroid dehydrogenase | 4 | NAD+ | 0.77 | cholic acid[1] | 49 | 28.5 |
| 7α-hydroxy-steroid dehydrogenase | 4 | NAD+ | 0.77 | cholic acid[1] | 49 | 17.2% |
| 12α-hydroxy-steroid dehydrogenase/ 7α-hydroxy-steroid dehydrogenase | 5/2.3 | NAD+ | 0.28 | cholic acid[2] | 51.5 | 91% |
| 12α-hydroxy-steroid dehydrogenase/ 7α-hydroxy-steroid dehydrogenase/ oxidase | 5/2.3/1.3 | NAD+ | 0.28 | cholic acid[2] | 51.5 | 100% |
| NADH dependent alcohol dehydrogenase/ 6.75 mg hydroxylase | 6 | NAD+ | 0.19 | 2.3-butanediol | 427 | 98% |
| NADPH dependent alcohol dehydrogenase/ 6.75 mg hydroxylase | 2 | NADP+ | 0.19 | 2-propanol | 909 | 100% |
| formate dehydrogenase | 4 | NAD+ | 0.82 | Na formate | 204 | 21.5% |

[1]Used as a 20% cholic acid solution

[2]Used as a bile acid solution (237 mM cholic acid; 45 mM deoxycholic acid)

Example 8: Quantitative LCA (Lithocholic Acid) Conversion

Reaction mixture:

- 10 μl 10 mM NAD+
- 250 μl 100 mM TEA pH 8.2
- 10 mM (final) lithocholic acid
- 9.2 mg cells (wW) as a 22.5% suspension in 100 mM TEA pH 8.0 and 25% glycerin
- 5 μl catalase (bovine, Sigma 4 mg/ml)
- 1.7 units xylitol/sorbitol dehydrogenase
- 25 μl 2M sorbitol (final 100 mM)
- 176 μl $dH_2O$ The reactions were set up in 1.5 ml screw-top bottles and sealed with lids with aluminium foil. The foil was punctured in several places. It was gently shaken at 24° C. for 18 h.

The recovery of NADH was effected by sorbitol or, respectively, xylitol dehydrogenase in the presence of sorbitol and $NAD^+$.

200 μl of the reaction batch was diluted with 600 μl acetonitrile/5 μl $H_3PO_4$ (50%) and incubated at 55° C. for 15 minutes. Subsequently, the samples were centrifuged at 20817 rcf for 5 minutes and analyzed using HPLC/DAD (e.g., Agilent 1200 series; column: Merck Purospher STAR RP-18e 125×4 mm or Agilent Zorbax XDB-$C_8$ mm 150×4.6 mm, 3.5 μm, 5 μm; flow rate: 1.5 ml/min, gradient $H_2O$+$H_3PO_4$ (pH=2.6)/acetonitrile).

Under the above-mentioned conditions, only ursodeoxycholic acid was detected after the conversion.

Example 9: Conversion of LCA (Lithocholic Acid) to Ursodeoxycholic Acid in the Presence of Organic Solvents At first, the solubility limits of LCA and UDCA in various organic solvents were determined. For this purpose, 10 mg or, respectively, 100 mg of LCA or UDCA was placed in a 15 mL flask. The organic solvent was added in increments of 100 μL, and the mixture was treated by shaking in a vortex shaker and optionally in an ultrasonic bath. It was visually assessed as to whether a clear solution was present.

The following table summarizes the solubility limits determined for the analyzed solvents:

| Solvent | UDCA [mg/ml] | LCA [mg/ml] |
|---|---|---|
| methanol | >100.0 | 28.6 |
| ethanol | 54.5 | 32.3 |
| isopropanol (IPA) | 47.5 | 33.7 |
| ethylene glycol | 16.6 | <1.0 |
| ethyl acetate (EtOAc) | 2.9 | 2.9 |
| methyl isobutyl ketone (MIBK) | 4.4 | 4.3 |
| methyl isobutyl alcohol (MIBA) | 35.7 | 33.7 |
| DMSO | >500.0 | 103.8 |
| DMF | >500.0 | 248.0 |
| DMA | >500.0 | >500.0 |
| hexane/EtOAc + 0.01% trifluoroacetic acid (TFA) | <0.8 | 1.4 |
| hexane/IPA 8:2 + 0.01% TFA | 4.0 | 6.7 |
| hexane/IPA 7:3 + 0.02% TFA | 12.0 | 10.6 |
| cyclohexane | <0.7 | <0.6 |
| toluene | <1.0 | <1.0 |

-continued

| Solvent | UDCA [mg/ml] | LCA [mg/ml] |
|---|---|---|
| THF | 259.0 | 128.5 |
| Me—THF | 63.4 | 64.8 |
| dioxane | 92.6 | 51.4 |
| $Et_2O$ | 2.0 | 3.4 |
| i $Pr_2O$ | <0.5 | 0.9 |
| 2-butanol | 53.0 | 34.3 |
| 2-butanone | 10.0 | 10.0 |
| acetone | 8.8 | 4.9 |
| $CHCl_3$ | 2.9 | 4.9 |
| $CHCl_3$/phenol | 21.3 | 18.2 |
| $CH_2Cl_2$ | 1.1 | 1.4 |

The conversion of LCA to UDCA in the presence of the solvents was determined as indicated in the following tables:

| Solvent | conc. LCA [mg/ml] | conc. LCA [%] | conversion* | |
|---|---|---|---|---|
| EtOH | 4.3 | 0.4 | 4% | protic |
| MIBA | 4.3 | 0.4 | 3% | |
| DMSO | 4.4 | 0.4 | 31% | aprotic |
| | 4.8 | 0.5 | 32% | |
| | 5.6 | 0.6 | 41% | |
| | 7.4 | 0.7 | 48% | |
| | 11.0 | 1.1 | 52% | |
| | 14.8 | 1.5 | 45% | |
| | 17.4 | 1.7 | 9% | |
| | 21.8 | 2.2 | 7% | |
| DMF | 4.8 | 0.5 | 30% | |
| | 5.6 | 0.6 | 63% | |
| | 7.9 | 0.8 | 43% | |
| | 10.0 | 1.0 | 70% | |
| | 11.3 | 1.1 | 48% | |
| | 16.9 | 1.7 | 42% | |
| | 22.5 | 2.3 | 35% | |
| | 28.2 | 2.8 | 28% | |
| DMA | 3.7 | 0.4 | 22% | |
| | 5.9 | 0.6 | 41% | |
| | 7.9 | 0.8 | 44% | |
| | 11.9 | 1.2 | 51% | |
| | 13.6 | 1.4 | 53% | |
| | 16.5 | 1.7 | 50% | |
| | 22.4 | 2.2 | 6% | |

-continued

| Solvent | conc. LCA [mg/ml] | conc. LCA [%] | conversion* |
|---|---|---|---|
| | 30.0 | 3.0 | 4% |
| | 37.4 | 3.7 | 3% |
| Me—THF | 4.8 | 0.5 | 8% |
| THF | 4.8 | 0.5 | 7% |
| | 9.9 | 1.0 | 12% |
| | 13.2 | 1.3 | 14% |
| | 19.7 | 2.0 | 17% |

Example 10: Conversion of Lithocholic Acid to Ursodeoxycholic Acid with Increased Substrate Concentration in the Presence of an Aprotic Solvent Reaction mixture:

10 µl 10 mM NAD+
250 µl 200 mM TEA pH 8.4 with 10.8% glycerin
25 µl 500 mM lithocholic acid in DMF
30 mg cells (wW) as a 30% suspension in 100 mM TEA pH 9.0
5 µl catalase (bovine, Sigma 4 mg/ml)
1.7 units xylitol/sorbitol dehydrogenase
25 µl 2M sorbitol (final 100 mM)
73 µl $dH_2O$ The reactions were set up in 1.5 ml screw-top bottles and sealed with lids with aluminium foil. The foil was punctured in several places. It was gently shaken at 24° C. for 18 h.

The recovery of NADH was effected by sorbitol or, respectively, xylitol dehydrogenase in the presence of sorbitol and $NAD^+$.

The reaction batch was completely evaporated in a stream of air and redissolved with 1.1 ml IPA+0.5% TFA. Subsequently, the samples were centrifuged at 20817 rcf for 5 minutes, and the supernatant was analyzed by HPLC/RID (e.g., Agilent 1200 series; column: Phenomenex Luna® Silica 100 Å, 250×4.6 mm, 5 µm; flow rate: 1.0 ml/min, n-hexane/IPA 4:1+0.05% TFA isocratic).

Under the above-mentioned conditions, 70% ursodeoxycholic acid was detected after the conversion.

The invention claimed is:

1. A method of preparing a steroid having the general formula (I):

(I)

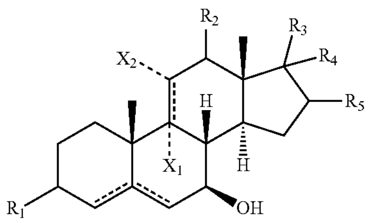

wherein $X_1$ and $X_2$ are independently H, Cl, F, Br, I, $CF_3$, a $C_1$ to $C_6$ alkyl radical, OH, a $C_1$ to $C_6$ alkoxy radical, CN, $NO_2$, $N(R_6)_2$, an epoxy group, CHO, or a $CO_2R_6$ radical, wherein $R_6$ is —C(O)H, —$C(O)CH_3$, —$C(O)CH_2CH_3$, —$C(O)(CH_2)_2CH_3$, —$C(O)CH(CH_3)_2$, —$C(O)(CH_2)_3CH_3$, —$C(O)CH(CH_3)CH_2CH_3$, —$C(O)CH_2CH(CH_3)_2$, —$C(O)C(CH_3)_3$, —C(O)Ph, or —$C(O)CH_2Ph$, $R_1$ and $R_2$ are independently H, OH, $OR_7$ or O, wherein $R_7$ is —C(O)H, —$C(O)CH_3$, —$C(O)CH_2CH_3$, —$C(O)(CH_2)_2CH_3$, —$C(O)CH(CH_3)_2$, —$C(O)(CH_2)_3CH_3$, —$C(O)CH(CH_3)CH_2CH_3$, —$C(O)CH_2CH(CH_3)_2$, —$C(O)C(CH_3)_3$, —C(O)Ph, or —$C(O)CH_2Ph$, $R_3$ is H, OH, $OR_8$, a $C_1$ to $C_{10}$ alkyl radical, a $C_1$ to $C_{10}$ alkenyl radical, —CHO, —$C(O)(CH_3)$, —$C(O)(CH_2OH)$, —$CH(CH_3)C(O)CH_3$, —$CH(CH_3)((CH_2)_2CO_2R_9)$, or —$CH(CH_3)((CH_2)_2CONHR_9)$, wherein $R_8$ is —C(O)H, —$C(O)CH_3$, —$C(O)CH_2CH_3$, —$C(O)(CH_2)_2CH_3$, —$C(O)CH(CH_3)_2$, —$C(O)(CH_2)_3CH_3$, —$C(O)CH(CH_3)CH_2CH_3$, —$C(O)CH_2CH(CH_3)_2$, —$C(O)C(CH_3)_3$, —C(O)Ph, or —$C(O)CH_2Ph$, and $R_9$ is —$CH_3$, —$CH_2COOH$, —$CH_2CH_3$, —$CH(CH_3)_2$, —$(CH_2)_2CH_3$, —$(CH_2)_2SO_3H$, $C(CH_3)_3$, —$(CH_2)_3CH_3$, —$CH(CH_3)CH_2CH_3$, —$CH_2CH(CH_3)_2$, an aryl group, or an alkylaryl group, $R_4$ is H, OH, or —$OR_{10}$, wherein $R_{10}$ is —C(O)H, —$C(O)CH_3$, —$C(O)CH_2CH_3$, —$C(O)(CH_2)_2CH_3$, —$C(O)CH(CH_3)_2$, —$C(O)(CH_2)_3CH_3$, —$C(O)CH(CH_3)CH_2CH_3$, —$C(O)CH_2CH(CH_3)_2$, —$C(O)C(CH_3)_3$, —C(O)Ph, or —$C(O)CH_2Ph$, and $R_5$ is H, $CF_3$, a $C_1$ to $C_6$ alkyl radical, a $C_1$ to Co alkenyl radical, OH, O, or a $C_1$ to $C_6$ alkoxy radical, wherein the dashed line denotes an optional double bond, with the proviso that the B ring has no double bond if the A ring has a $C_4$-$C_5$ double bond, and the C ring has no double bond if $X_1$ and $X_2$ form an epoxy group, or wherein the steroid having general formula (I) is selected from the group consisting of 3α,7β, 12α-trihydroxy-5β-cholane-24-acid, 3α,7β, 12β-trihydroxy-5β-cholane-24-acid, 3β, 7β, 12α-trihydroxy-5β-cholane-24-acid, 3β, 7β, 12β-trihydroxy-5β-cholane-24-acid, 7β, 12α-dihydroxy-3-keto-5β-cholane-24-acid, 7β, 12β-dihydroxy-3-keto-5β-cholane-24-acid, 3α,7β-dihydroxy-12-keto-5β-cholane-24-acid, 3β, 7β-diydroxy-12-keto-5β-cholane-24-acid, 7β-hydroxy-3,12-diketo-5β-cholane-24-acid, 3α,7β-dihydroxy-5β-cholane-24-acid, 7β-hydroxy-3-keto-5β-cholane-24-acid and 3β, 7β-dihydroxy-5β-cholane-24-acid, the method comprising the step of converting a 7-deoxysteroid selected from the group consisting of 3α,12α-dihydroxy-5β-cholane-24-acid, 3α,12β-dihydroxy-5β-cholane-24-acid, 3β,12α-dihydroxy-5β-cholane-24-acid, 3β,12β-dihydroxy-5β-cholane-24-acid, 3β-hydroxy-12-keto-5β-cholane-24-acid, 3-keto, 12β-hydroxy-5β-cholane-24-acid, 3α-hydroxy-12-keto-5β-cholane-24-acid, 3-keto, 12α-hydroxy-5β-cholane-24-acid, 3,12-diketo-5β-cholane-24-acid, 3α-hydroxy-5β-cholane-24-acid, 3-keto-5β-cholane-24-acid and 3β-hydroxy-5β-cholane-24-acid or having the general formula (II) with a cytochrome P450 hydroxylase or a functional variant thereof in the presence of at least one redox partner system and a system for regenerating the redox partner system:

(II)

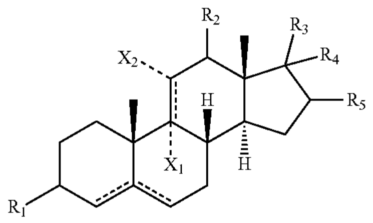

wherein $X_1$, $X_2$, $R_1$, $R_2$, $R_3$, $R_4$, and $R_5$ in Formula II are as defined in Formula I, wherein the cytochrome P450 hydroxylase comprises an amino acid sequence which is at least 90% identical to the amino acid sequence of SEQ ID No. 1 or SEQ ID No. 2.

2. A method according to claim 1, wherein $X_1$, $X_2$, $R_4$ and $R_5$ are H, and $R_1$ and $R_2$ are independently H, OH, $OR_7$ or O, wherein $R_7$ is —C(O)H, —$C(O)CH_3$, —$C(O)CH_2CH_3$, —$C(O)(CH_2)_2CH_3$, —$C(O)CH(CH_3)_2$, —$C(O)(CH_2)_3CH_3$, —$C(O)CH(CH_3)CH_2CH_3$, —$C(O)CH_2CH(CH_3)_2$, —$C(O)C(CH_3)_3$, —C(O)Ph, or —$C(O)CH_2Ph$, $R_3$ is a $C_1$ to $C_{10}$ alkyl radical, a $C_1$ to $C_{10}$ alkenyl radical, —$CH(CH_3)((CH_2)_2CO_2R_9)$, or —$CH(CH_3)((CH_2)_2CONHR_9)$, wherein $R_9$ is —$CH_3$, —$CH_2COOH$, —$CH_2CH_3$, —$CH(CH_3)_2$, —$(CH_2)_2CH_3$, —$(CH_2)_2SO_3H$, $C(CH_3)_3$, —$(CH_2)_3CH_3$, —$CH(CH_3)CH_2CH_3$, —$CH_2CH(CH_3)_2$, an aryl group, or an alkylaryl group.

3. A method according to claim 1, wherein the aryl group is selected from the group consisting of a phenyl radical, a phenyl radical substituted with F, Cl, Br, $NO_2$ or $CH_3$, and a heteroaryl.

4. A method according to claim 1, wherein the alkylaryl group is selected from the group consisting of a benzyl group, a halogenated benzyl group, wherein the halogen is F, Cl or Br, and a benzyl group substituted with $NO_2$.

5. A method according to claim 1, wherein $R_1$ is OH, $R_2$ is O, or OH, $R_3$ is —$CH(CH_3)((CH_2)_2CO_2R_9)$, $R_4$ is H, and $R_5$ is H.

6. A method according to claim 1, wherein the cytochrome P450 hydroxylase is encoded by a nucleic acid which is at least 90% identical to the nucleic acid sequence SEQ ID No. 3, SEQ ID No. 4, SEQ ID No. 5, or SEQ ID No. 6.

7. A method according to claim 1, wherein the at least one redox partner system comprises:

(i) ferredoxin, ferredoxin reductase, and NAD(P)H;

(ii) cytochrome P450 reductase and NAD(P)H; or (iii) NAD(P)H.

8. A method according to claim 7, wherein the ferredoxin is selected from the group consisting of adrenodoxins, putidaredoxins, and flavodoxins.

9. A method according to claim 7, wherein the at least one ferredoxin reductase is selected from the group of flavodoxin reductases and putidaredoxin reductase.

10. A method according to claim 1, wherein the system for the regeneration of the redox partner system comprises at least one oxidoreductase and at least one substrate of the at least one oxidoreductase.

11. A method according to claim 10, wherein the at least one oxidoreductase is selected from the group consisting of oxidoreductase (EC: 1.1.1), aldehyde dehydrogenase (EC: 1.2.1), amino acid dehydrogenase (EC: 1.4.1), flavin reductase (EC: 1.5.1), transhydrogenase (EC: 1.6.1), nitrite reductase (EC: 1.7.1) and phosphonate dehydrogenase (EC: 1.20.1), preferably selected from the group consisting of alcohol dehydrogenase, hydroxysteroid dehydrogenase, phosphite dehydrogenase, and sugar dehydrogenase.

12. A method according to claim 10, wherein the at least one oxidoreductase is selected from the group consisting of glucose dehydrogenase, glucose-6-phosphate dehydrogenase, arabinose dehydrogenase, xylose dehydrogenase, sorbitol dehydrogenase, xylitol dehydrogenase, 12α-hydroxysteroid dehydrogenase, 7α-hydroxysteroid dehydrogenase, 20α-hydroxysteroid dehydrogenase, 17β-hydroxysteroid dehydrogenase, 17α-hydroxysteroid dehydrogenase, 3α-hydroxysteroid dehydrogenase, 3β-hydroxy-delta5 dehydrogenase, 11β-hydroxysteroid dehydrogenase, and formate dehydrogenase.

13. A method according to claim 10, wherein the at least one substrate of the at least one oxidoreductase is selected from the group consisting of arabinose, xylose, glucose, sorbitol, xylitol, cholane-24-acid, 3α,12α-dihydroxy-cholane-24-acid-2,3-butanediol, acetoin, 2-propanol, glutamates, ethanol, phosphonates, phosphites, nitrites, 4-methyl-2-pentanol, 2-butanol, 2-octanol, cyclohexanol, ethanediol, 1,2-propanediol, 1-propanol, 1-butanol, and formate, 3-hydroxybutanoate.

14. A method according claim 1, wherein the method is performed in the presence of at least one organic solvent.

15. A method according to claim 14, wherein the at least one organic solvent is a protic or aprotic solvent.

16. A method according to claim 14, wherein the at least one organic solvent is selected from the group consisting of dimethylformamide (DMF), dimethyl sulfoxide (DMSO), and dimethylacetamide (DMA).

17. The method according to claim 1, wherein the cytochrome P450 hydroxylase comprises an amino acid sequence which is 100% identical to the amino acid sequence of SEQ ID No. 1 or SEQ ID No. 2.

18. A method according to claim 15, wherein the at least one organic solvent is an aprotic solvent.

* * * * *

SEQUENCE LISTING

```
<160> NUMBER OF SEQ ID NOS: 12

<210> SEQ ID NO 1
<211> LENGTH: 397
<212> TYPE: PRT
<213> ORGANISM: Streptomyces hygroscopicus

<400> SEQUENCE: 1

Met Leu Thr Thr Ala Glu Thr Thr Ser Ile Ala Tyr Pro Phe Asn Thr
1               5                   10                  15

Ala Glu Gly Leu Ala Leu Ser Glu Arg Tyr Glu Glu Ala Arg Asn Arg
            20                  25                  30

Thr Gly Leu Leu Arg Val Arg Met Pro Tyr Gly Glu Pro Ala Trp Leu
        35                  40                  45

Val Thr Arg Tyr Ala Asp Ala Arg Leu Val Leu Gly Asp Arg Arg Phe
    50                  55                  60

Ser Arg Ala Glu Ala Leu His His Asp Glu Pro Arg Gln Ser Glu Gly
65                  70                  75                  80
```

-continued

```
Arg Arg Asp Ser Gly Ile Leu Thr Met Asp Pro Pro Asp His Thr Arg
                85                  90                  95

Leu Arg Thr Leu Val Ala Lys Ala Phe Thr Val His Gln Val Glu Lys
            100                 105                 110

Leu Arg Pro Trp Val Arg Gln Leu Thr His Asp Leu Leu Asp Asp Leu
        115                 120                 125

Glu Ala Ala Gly Pro Pro Ala Asp Leu Val Asp Arg Tyr Ala Leu Pro
    130                 135                 140

Ile Pro Val Gly Val Ile Cys Ala Met Leu Gly Val Pro Gln Glu Asp
145                 150                 155                 160

Arg Pro Lys Phe Arg Val Trp Ser Asp Ala Ala Leu Ser Thr Ser Ser
                165                 170                 175

Leu Ser Ala Glu Gln Phe Ala Arg Asn Thr Asp Glu Leu Arg Ala Tyr
            180                 185                 190

Met Ala Gly Leu Ile Glu Asp His Arg Arg Thr Pro Arg Asp Asp Ile
        195                 200                 205

Met Thr Ser Leu Ile Glu Ala Arg Asp Ala Gly Asp Arg Leu Ser Glu
    210                 215                 220

Leu Glu Leu Val Asp Leu Cys Val Gly Ile Leu Val Ala Gly His Glu
225                 230                 235                 240

Thr Thr Ala Thr Gln Ile Pro Asn Phe Val Leu Thr Leu Leu Glu His
                245                 250                 255

Pro Asp Gln Leu Arg Arg Leu Arg Glu Asp Pro Ala Leu Ile Gln Gly
            260                 265                 270

Ala Val Glu Glu Leu Leu Arg Phe Val Pro Leu Gly Val Gly Ala Ala
        275                 280                 285

Gln Ala Arg Tyr Ala Thr Glu Asp Ile Glu Val Gly Gly Thr Leu Val
    290                 295                 300

Arg Ser Gly Glu Pro Val Leu Val Ala Val Gly Ser Ala Asn Arg Asp
305                 310                 315                 320

Ala Leu Arg Phe Asp Glu Pro Gly Val Leu Asn Val Ala Arg Pro Thr
                325                 330                 335

Thr Gln His Leu Gly Phe Gly His Gly Val His His Cys Leu Gly Ala
            340                 345                 350

Pro Leu Ala Arg Leu Glu Leu Gln Glu Ala Leu Gly Ala Leu Ile Thr
        355                 360                 365

Arg Phe Pro Gly Leu Arg Leu Ala Gly Asp Ile Glu Trp Lys Asp Arg
    370                 375                 380

Met Leu Val Arg Gly Pro Arg Val Met Pro Ile Gly Trp
385                 390                 395
```

<210> SEQ ID NO 2
<211> LENGTH: 358
<212> TYPE: PRT
<213> ORGANISM: Streptomyces hygroscopicus

<400> SEQUENCE: 2

```
Met Pro Tyr Gly Glu Pro Ala Trp Leu Val Thr Arg Tyr Ala Asp Ala
1               5                   10                  15

Arg Leu Val Leu Gly Asp Arg Arg Phe Ser Arg Ala Glu Ala Leu His
            20                  25                  30

His Asp Glu Pro Arg Gln Ser Glu Gly Arg Arg Asp Ser Gly Ile Leu
        35                  40                  45

Thr Met Asp Pro Pro Asp His Thr Arg Leu Arg Thr Leu Val Ala Lys
    50                  55                  60
```

-continued

Ala Phe Thr Val His Gln Val Glu Lys Leu Arg Pro Trp Val Arg Gln
65 70 75 80

Leu Thr His Asp Leu Leu Asp Asp Leu Glu Ala Ala Gly Pro Pro Ala
85 90 95

Asp Leu Val Asp Arg Tyr Ala Leu Pro Ile Pro Val Gly Val Ile Cys
100 105 110

Ala Met Leu Gly Val Pro Gln Glu Asp Arg Pro Lys Phe Arg Val Trp
115 120 125

Ser Asp Ala Ala Leu Ser Thr Ser Ser Leu Ser Ala Glu Gln Phe Ala
130 135 140

Arg Asn Thr Asp Glu Leu Arg Ala Tyr Met Ala Gly Leu Ile Glu Asp
145 150 155 160

His Arg Arg Thr Pro Arg Asp Asp Ile Met Thr Ser Leu Ile Glu Ala
165 170 175

Arg Asp Ala Gly Asp Arg Leu Ser Glu Leu Glu Leu Val Asp Leu Cys
180 185 190

Val Gly Ile Leu Val Ala Gly His Glu Thr Thr Ala Thr Gln Ile Pro
195 200 205

Asn Phe Val Leu Thr Leu Leu Glu His Pro Asp Gln Leu Arg Arg Leu
210 215 220

Arg Glu Asp Pro Ala Leu Ile Gln Gly Ala Val Glu Glu Leu Leu Arg
225 230 235 240

Phe Val Pro Leu Gly Val Gly Ala Ala Gln Ala Arg Tyr Ala Thr Glu
245 250 255

Asp Ile Glu Val Gly Gly Thr Leu Val Arg Ser Gly Glu Pro Val Leu
260 265 270

Val Ala Val Gly Ser Ala Asn Arg Asp Ala Leu Arg Phe Asp Glu Pro
275 280 285

Gly Val Leu Asn Val Ala Arg Pro Thr Thr Gln His Leu Gly Phe Gly
290 295 300

His Gly Val His His Cys Leu Gly Ala Pro Leu Ala Arg Leu Glu Leu
305 310 315 320

Gln Glu Ala Leu Gly Ala Leu Ile Thr Arg Phe Pro Gly Leu Arg Leu
325 330 335

Ala Gly Asp Ile Glu Trp Lys Asp Arg Met Leu Val Arg Gly Pro Arg
340 345 350

Val Met Pro Ile Gly Trp
355

<210> SEQ ID NO 3
<211> LENGTH: 1194
<212> TYPE: DNA
<213> ORGANISM: Streptomyces hygroscopicus

<400> SEQUENCE: 3
atgttgacca cagccgagac gacatccatc gcctatccct tcaacaccgc cgaagggctg 60
gcgctcagcg agcgttacga agaggccagg aaccgcaccg gactgctccg ggtgcggatg 120
ccctacggtg agcccgcctg gctggtcacg cggtacgccg acgcccggct ggtgctcggc 180
gaccggcgct tcagccgtgc ggaggcgctc caccacgacg agccgcggca gtccgaaggc 240
cggcgcgaca gcggcatcct gaccatggac ccgcccgacc acacccggct gcgcaccctc 300
gtcgccaagg cgttcaccgt ccaccaggtg gagaaactcc gcccctgggt acgccagttg 360
acccatgacc tgctcgacga cctcgaggcc gccgggccgc ccgccgatct ggtggaccgc 420

-continued

```
tacgccctgc ccattccggt cggcgtcatc tgcgccatgc tcggcgtccc gcaggaggac    480

cggcccaagt tccgggtctg gagcgacgcc gcgctgtcca ccagctcgct gagcgccgag    540

cagttcgccc gtaacaccga cgagctgcgc gcctacatgg ccgggctgat cgaggaccac    600

cgcaggaccc cgcgggacga catcatgacc tcgctgatcg aggcgcggga cgcgggcgac    660

cggctgtccg agctggaact cgtcgatctg tgcgtgggca tcctggtggc cgggcacgag    720

accaccgcca cccagatccc caacttcgtg ctgacgctgc tggagcaccc ggaccagctg    780

cgccggctgc gcgaggaccc cgccctgatc cagggcgccg tcgaggagct gctgcgcttc    840

gtcccgctgg gcgtgggcgc cgcccaggcc cgttacgcca ccgaggacat cgaggtgggc    900

ggcacgctgg tgcgcagcgg ggagccggtg ctggtcgccg tcggctcggc caaccgcgac    960

gcgctgcgct tcgacgaacc gggcgtgctc aacgtcgccc gccccaccac ccagcacctc   1020

ggcttcggcc acggtgtgca ccactgcctg ggcgcgcccc tggcccgtct ggagctccag   1080

gaggcgctcg gcgcgctgat cacgcgcttc ccgggcctgc ggctggccgg ggacatcgag   1140

tggaaggacc gcatgctggt ccgcgggccc cgtgtcatgc ccatcgggtg gtga         1194
```

<210> SEQ ID NO 4
<211> LENGTH: 1077
<212> TYPE: DNA
<213> ORGANISM: Streptomyces hygroscopicus

<400> SEQUENCE: 4

```
atgccctacg gtgagcccgc ctggctggtc acgcggtacg ccgacgcccg gctggtgctc     60

ggcgaccggc gcttcagccg tgcggaggcg ctccaccacg acgagccgcg gcagtccgaa    120

ggccggcgcg acagcggcat cctgaccatg gacccgcccg accacacccg gctgcgcacc    180

ctcgtcgcca aggcgttcac cgtccaccag gtggagaaac tccgcccctg ggtacgccag    240

ttgacccatg acctgctcga cgacctcgag gccgccgggc cgcccgccga tctggtggac    300

cgctacgccc tgcccattcc ggtcggcgtc atctgcgcca tgctcggcgt cccgcaggag    360

gaccggccca agttccgggt ctggagcgac gccgcgctgt ccaccagctc gctgagcgcc    420

gagcagttcg cccgtaacac cgacgagctg cgcgcctaca tggccgggct gatcgaggac    480

caccgcagga ccccgcggga cgacatcatg acctcgctga tcgaggcgcg ggacgcgggc    540

gaccggctgt ccgagctgga actcgtcgat ctgtgcgtgg gcatcctggt ggccgggcac    600

gagaccaccg ccacccagat ccccaacttc gtgctgacgc tgctggagca cccggaccag    660

ctgcgccggc tgcgcgagga ccccgccctg atccagggcg ccgtcgagga gctgctgcgc    720

ttcgtcccgc tgggcgtggg cgccgcccag gcccgttacg ccaccgagga catcgaggtg    780

ggcggcacgc tggtgcgcag cggggagccg gtgctggtcg ccgtcggctc ggccaaccgc    840

gacgcgctgc gcttcgacga accgggcgtg ctcaacgtcg cccgccccac cacccagcac    900

ctcggcttcg gccacggtgt gcaccactgc ctgggcgcgc ccctggcccg tctggagctc    960

caggaggcgc tcggcgcgct gatcacgcgc ttcccgggcc tgcggctggc cggggacatc   1020

gagtggaagg accgcatgct ggtccgcggg ccccgtgtca tgcccatcgg gtggtga      1077
```

<210> SEQ ID NO 5
<211> LENGTH: 1194
<212> TYPE: DNA
<213> ORGANISM: Artificial Sequence
<220> FEATURE:
<223> OTHER INFORMATION: E.coli Codon-optimized SEQ ID No. 3

-continued

<400> SEQUENCE: 5

```
atgctgacca ccgcagaaac caccagtatt gcatatccgt ttaataccgc agaaggtctg     60
gcactgagcg aacgttatga agaagcacgt aatcgtaccg gtctgctgcg tgttcgtatg    120
ccgtatggtg aaccggcatg gctggttacc cgttatgcag atgcccgtct ggttctgggt    180
gatcgtcgtt ttagccgtgc cgaagcactg catcacgatg aaccgcgtca gagcgaaggt    240
cgtcgtgata gcggtattct gaccatggat ccgcctgatc atacccgtct gcgtaccctg    300
gttgcaaaag catttaccgt tcatcaggtt gaaaaactgc gtccgtgggt tcgccagctg    360
acccatgatc tgctggatga tctggaagca gcaggtccgc ctgcagatct ggttgatcgt    420
tatgcactgc cgattccggt tggtgttatt tgtgcaatgc tgggtgttcc gcaagaagat    480
cgtcctaaat ttcgtgtttg gagtgatgca gcactgagca ccagcagcct gagcgcagaa    540
cagtttgcac gtaataccga tgaactgcgt gcatatatgg caggtctgat tgaagatcat    600
cgtcgtacac cgcgtgatga tattatgacc agcctgatcg aagcacgtga tgccggtgat    660
cgcctgagtg aactggaact ggtggatctg tgtgttggta ttctggttgc aggtcatgaa    720
accaccgcaa cccagattcc gaattttgtt ctgaccctgc tggaacatcc ggatcagctg    780
cgtcgtctgc gtgaagatcc ggcactgatt cagggtgcag ttgaagaact gctgcgtttt    840
gttccgctgg gtgtgggtgc agcacaggca cgttatgcaa ccgaagatat tgaagttggt    900
ggcaccctgg ttcgtagtgg cgaaccggtg ctggttgccg ttggtagcgc aaaccgtgat    960
gcactgcgct ttgatgaacc gggtgttctg aatgttgcac gtccgaccac acagcatctg   1020
ggttttggtc atggtgttca tcattgtctg ggtgcaccgc tggcacgtct ggaactgcaa   1080
gaagcactgg gagcactgat tacccgtttt ccgggtctgc gtctggcagg cgatattgaa   1140
tggaaagatc gtatgctggt tcgtggtccg cgtgttatgc cgattggttg gtaa         1194
```

<210> SEQ ID NO 6
<211> LENGTH: 1070
<212> TYPE: DNA
<213> ORGANISM: Artificial Sequence
<220> FEATURE:
<223> OTHER INFORMATION: E.coli Codon-optimized SEQ ID No. 4

<400> SEQUENCE: 6

```
atggtgaacc ggcatggctg gttacccgtt atgcagatgc ccgtctggtt ctgggtgatc     60
gtcgttttag ccgtgccgaa gcactgcatc acgatgaacc gcgtcagagc gaaggtcgtc    120
gtgatagcgg tattctgacc atggatccgc ctgatcatac ccgtctgcgt accctggttg    180
caaaagcatt taccgttcat caggttgaaa aactgcgtcc gtgggttcgc cagctgaccc    240
atgatctgct ggatgatctg gaagcagcag gtccgcctgc agatctggtt gatcgttatg    300
cactgccgat tccggttggt gttatttgtg caatgctggg tgttccgcaa gaagatcgtc    360
ctaaatttcg tgtttggagt gatgcagcac tgagcaccag cagcctgagc gcagaacagt    420
ttgcacgtaa taccgatgaa ctgcgtgcat atatggcagg tctgattgaa gatcatcgtc    480
gtacaccgcg tgatgatatt atgaccagcc tgatcgaagc acgtgatgcc ggtgatcgcc    540
tgagtgaact ggaactggtg gatctgtgtg ttggtattct ggttgcaggt catgaaacca    600
ccgcaaccca gattccgaat tttgttctga ccctgctgga acatccggat cagctgcgtc    660
gtctgcgtga agatccggca ctgattcagg gtgcagttga agaactgctg cgttttgttc    720
cgctgggtgt gggtgcagca caggcacgtt atgcaaccga agatattgaa gttggtggca    780
ccctggttcg tagtggcgaa ccggtgctgg ttgccgttgg tagcgcaaac cgtgatgcac    840
```

-continued

```
tgcgctttga tgaaccgggt gttctgaatg ttgcacgtcc gaccacacag catctgggtt    900

ttggtcatgg tgttcatcat tgtctgggtg caccgctggc acgtctggaa ctgcaagaag    960

cactgggagc actgattacc cgttttccgg gtctgcgtct ggcaggcgat attgaatgga   1020

aagatcgtat gctggttcgt ggtccgcgtg ttatgccgat tggttggtaa              1070


<210> SEQ ID NO 7
<211> LENGTH: 107
<212> TYPE: PRT
<213> ORGANISM: Pseudomonas putida
<220> FEATURE:
<221> NAME/KEY: VARIANT
<222> LOCATION: (1)..(1)
<223> OTHER INFORMATION: Xaa is Methionine or no amino acid

<400> SEQUENCE: 7

Xaa Ser Lys Val Val Tyr Val Ser His Asp Gly Thr Arg Arg Glu Leu
1               5                   10                  15

Asp Val Ala Asp Gly Val Ser Leu Met Gln Ala Ala Val Ser Asn Gly
            20                  25                  30

Ile Tyr Asp Ile Val Gly Asp Cys Gly Gly Ser Ala Ser Cys Ala Thr
        35                  40                  45

Cys His Val Tyr Val Asn Glu Ala Phe Thr Asp Lys Val Pro Ala Ala
    50                  55                  60

Asn Glu Arg Glu Ile Gly Met Leu Glu Cys Val Thr Ala Glu Leu Lys
65                  70                  75                  80

Pro Asn Ser Arg Leu Cys Cys Gln Ile Ile Met Thr Pro Glu Leu Asp
                85                  90                  95

Gly Ile Val Val Asp Val Pro Asp Arg Gln Trp
            100                 105


<210> SEQ ID NO 8
<211> LENGTH: 422
<212> TYPE: PRT
<213> ORGANISM: Pseudomonas putida

<400> SEQUENCE: 8

Met Asn Ala Asn Asp Asn Val Val Ile Val Gly Thr Gly Leu Ala Gly
1               5                   10                  15

Val Glu Val Ala Phe Gly Leu Arg Ala Ser Gly Trp Glu Gly Asn Ile
            20                  25                  30

Arg Leu Val Gly Asp Ala Thr Val Ile Pro His His Leu Pro Pro Leu
        35                  40                  45

Ser Lys Ala Tyr Leu Ala Gly Lys Ala Thr Ala Glu Ser Leu Tyr Leu
    50                  55                  60

Arg Thr Pro Asp Ala Tyr Ala Ala Gln Asn Ile Gln Leu Leu Gly Gly
65                  70                  75                  80

Thr Gln Val Thr Ala Ile Asn Arg Asp Arg Gln Gln Val Ile Leu Ser
                85                  90                  95

Asp Gly Arg Ala Leu Asp Tyr Asp Arg Leu Val Leu Ala Thr Gly Gly
            100                 105                 110

Arg Pro Arg Pro Leu Pro Val Ala Ser Gly Ala Val Gly Lys Ala Asn
        115                 120                 125

Asn Phe Arg Tyr Leu Arg Thr Leu Glu Asp Ala Glu Cys Ile Arg Arg
    130                 135                 140

Gln Leu Ile Ala Asp Asn Arg Leu Val Val Ile Gly Gly Gly Tyr Ile
145                 150                 155                 160
```

```
Gly Leu Glu Val Ala Ala Thr Ala Ile Lys Ala Asn Met His Val Thr
                165                 170                 175

Leu Leu Asp Thr Ala Ala Arg Val Leu Glu Arg Val Thr Ala Pro Pro
            180                 185                 190

Val Ser Ala Phe Tyr Glu His Leu His Arg Glu Ala Gly Val Asp Ile
        195                 200                 205

Arg Thr Gly Thr Gln Val Cys Gly Phe Glu Met Ser Thr Asp Gln Gln
    210                 215                 220

Lys Val Thr Ala Val Leu Cys Glu Asp Gly Thr Arg Leu Pro Ala Asp
225                 230                 235                 240

Leu Val Ile Ala Gly Ile Gly Leu Ile Pro Asn Cys Glu Leu Ala Ser
                245                 250                 255

Ala Ala Gly Leu Gln Val Asp Asn Gly Ile Val Ile Asn Glu His Met
            260                 265                 270

Gln Thr Ser Asp Pro Leu Ile Met Ala Val Gly Asp Cys Ala Arg Phe
        275                 280                 285

His Ser Gln Leu Tyr Asp Arg Trp Val Arg Ile Glu Ser Val Pro Asn
    290                 295                 300

Ala Leu Glu Gln Ala Arg Lys Ile Ala Ala Ile Leu Cys Gly Lys Val
305                 310                 315                 320

Pro Arg Asp Glu Ala Ala Pro Trp Phe Trp Ser Asp Gln Tyr Glu Ile
                325                 330                 335

Gly Leu Lys Met Val Gly Leu Ser Glu Gly Tyr Asp Arg Ile Ile Val
            340                 345                 350

Arg Gly Ser Leu Ala Gln Pro Asp Phe Ser Val Phe Tyr Leu Gln Gly
        355                 360                 365

Asp Arg Val Leu Ala Val Asp Thr Val Asn Arg Pro Val Glu Phe Asn
    370                 375                 380

Gln Ser Lys Gln Ile Ile Thr Asp Arg Leu Pro Val Glu Pro Asn Leu
385                 390                 395                 400

Leu Gly Asp Glu Ser Val Pro Leu Lys Glu Ile Ile Ala Ala Ala Lys
                405                 410                 415

Ala Glu Leu Ser Ser Ala
            420
```

<210> SEQ ID NO 9
<211> LENGTH: 324
<212> TYPE: DNA
<213> ORGANISM: Pseudomonas putida
<220> FEATURE:
<221> NAME/KEY: misc_feature
<222> LOCATION: (1)..(1)
<223> OTHER INFORMATION: n is A or no nucleotide
<220> FEATURE:
<221> NAME/KEY: misc_feature
<222> LOCATION: (2)..(2)
<223> OTHER INFORMATION: n is T or no nucleotide
<220> FEATURE:
<221> NAME/KEY: misc_feature
<222> LOCATION: (3)..(3)
<223> OTHER INFORMATION: n is G or no nucleotide

<400> SEQUENCE: 9

```
nnntctaaag tagtgtatgt gtcacatgat ggaacgcgtc gcgaactgga tgtggcggat      60

ggcgtcagcc tgatgcaggc tgcagtctcc aatggtatct acgatattgt cggtgattgt     120

ggcggcagcg ccagctgtgc cacctgccat gtctatgtga acgaagcgtt cacggacaag     180

gtgcccgccg ccaacgagcg ggaaatcggc atgctggagt gcgtcacggc cgaactgaag     240
```

ccgaacagca ggctctgctg ccagatcatc atgacgcccg agctggatgg catcgtggtc 300
gatgttcccg ataggcaatg gtaa 324

<210> SEQ ID NO 10
<211> LENGTH: 1269
<212> TYPE: DNA
<213> ORGANISM: Pseudomonas putida

<400> SEQUENCE: 10
atgaacgcaa acgacaacgt ggtcatcgtc ggtaccggac tggctggcgt tgaggtcgcc 60
ttcggcctgc gcgccagcgg ctgggaaggc aatatccggt tggtggggga tgcgacggta 120
attccccatc acctaccacc gctatccaaa gcttacttgg ccggcaaagc cacagcggaa 180
agcctgtacc tgagaacccc agatgcctat gcagcgcaga acatccaact actcggaggc 240
acacaggtaa cggctatcaa ccgcgaccga cagcaagtaa tcctatcgga tggccgggca 300
ctggattacg accggctggt attggctacc ggagggcgtc caagacccct accggtggcc 360
agtggcgcag ttggaaaggc gaacaacttt cgatacctgc gcacactcga ggacgccgag 420
tgcattcgcc ggcagctgat tgcggataac cgtctggtgg tgattggtgg cggctacatt 480
ggccttgaag tggctgccac cgccatcaag gcgaacatgc acgtcaccct gcttgatacg 540
gcagcccggg ttctggagcg ggttaccgcc ccgccggtat cggcctttta cgagcaccta 600
caccgcgaag ccggcgttga catacgaacc ggcacgcagg tgtgcgggtt cgagatgtcg 660
accgaccaac agaaggttac tgccgtcctc tgcgaggacg gcacaaggct gccagcggat 720
ctggtaatcg ccgggattgg cctgatacca aactgcgagt tggccagtgc ggccggcctg 780
caggttgata acggcatcgt gatcaacgaa cacatgcaga cctctgatcc cttgatcatg 840
gccgtcggcg actgtgcccg atttcacagt cagctctatg accgctgggt gcgtatcgaa 900
tcggtgccca atgccttgga gcaggcacga aagatcgccg ccatcctctg tggcaaggtg 960
ccacgcgatg aggcggcgcc ctggttctgg tccgatcagt atgagatcgg attgaagatg 1020
gtcggactgt ccgaagggta cgaccggatc attgtccgcg gctctttggc gcaacccgac 1080
ttcagcgttt tctacctgca gggagaccgg gtattggcgg tcgatacagt gaaccgtcca 1140
gtggagttca accagtcaaa acaaataatc acggatcgtt tgccggttga accaaaccta 1200
ctcggtgacg aaagcgtgcc gttaaaggaa atcatcgccg ccgccaaagc tgaactgagt 1260
agtgcctga 1269

<210> SEQ ID NO 11
<211> LENGTH: 327
<212> TYPE: DNA
<213> ORGANISM: Artificial Sequence
<220> FEATURE:
<223> OTHER INFORMATION: E.coli Codon-optimized SEQ ID No. 9
<220> FEATURE:
<221> NAME/KEY: misc_feature
<222> LOCATION: (1)..(1)
<223> OTHER INFORMATION: n is A or no nucleotide
<220> FEATURE:
<221> NAME/KEY: misc_feature
<222> LOCATION: (2)..(2)
<223> OTHER INFORMATION: n is T or no nucleotide
<220> FEATURE:
<221> NAME/KEY: misc_feature
<222> LOCATION: (3)..(3)
<223> OTHER INFORMATION: n is G or no nucleotide

<400> SEQUENCE: 11

-continued

```
nnnatgagca aagtggtcta tgtgtcgcat gatggaacac gccgtgagtt agacgtcgct     60

gatggtgtat ccctgatgca agcagcggtt agcaatggca tttacgacat cgttggcgat    120

tgtggtggta gtgcgtcatg tgcaacgtgt cacgtgtatg ttaacgaagc gtttaccgat    180

aaggtgcctg ctgccaatga acgcgagatt ggcatgctgg aatgcgtaac tgccgaactc    240

aaaccgaact ctcgcctgtg ctgccagatc atcatgaccc cggaattgga cgggattgtc    300

gttgatgtgc cagatcgtca gtggtaa                                        327


<210> SEQ ID NO 12
<211> LENGTH: 1269
<212> TYPE: DNA
<213> ORGANISM: Artificial Sequence
<220> FEATURE:
<223> OTHER INFORMATION: E.coli Codon-optimized SEQ ID No. 10

<400> SEQUENCE: 12

atgaacgcca atgataatgt tgttattgtt ggcaccggtc tggcaggcgt tgaagttgca     60

tttggtctgc gtgcaagcgg ttgggaaggt aatattcgtc tggttggtga tgcaaccgtt    120

attccgcatc atctgcctcc gctgagcaaa gcatatctgg caggtaaagc aaccgcagaa    180

agcctgtatc tgcgtacacc ggatgcctat gcagcacaga atattcagct gctgggtggt    240

acacaggtta ccgcaattaa tcgtgatcgt cagcaggtta ttctgagtga tggtcgtgca    300

ctggattatg atcgtctggt gctggcaacc ggtggtcgtc cgcgtccgct gccggttgca    360

agtggtgcag ttggtaaagc caataacttt cgttatctgc gcaccctgga agatgcagaa    420

tgtattcgtc gtcagctgat tgcagataat cgcctggttg tgattggtgg tggttatatt    480

ggtctggaag ttgcagcaac cgccattaaa gcaaatatgc atgttaccct gctggatacc    540

gcagcacgtg ttctggaacg tgttaccgca ccgcctgtta gcgcctttta tgaacatctg    600

catcgtgaag ccggtgttga tattcgtacc ggcacccagg tttgtggttt tgaaatgagc    660

accgatcagc agaaagttac cgcagttctg tgtgaagatg gcacccgtct gcctgcagat    720

ctggttattg caggtattgg cctgattccg aattgtgaac tggcaagcgc agcaggtctg    780

caggttgata atggtattgt tattaacgaa cacatgcaga ccagcgatcc gctgattatg    840

gcagttggtg attgtgcacg ttttcatagc cagctgtatg atcgttgggt tcgtattgaa    900

agcgttccga atgcactgga acaggcacgt aaaattgcag caattctgtg tggtaaagtt    960

ccgcgtgatg aagcagcacc gtggttttgg agcgatcagt atgaaattgg tctgaaaatg   1020

gttggtctga gcgaaggtta tgatcgcatt attgttcgtg gtagcctggc acagccggat   1080

ttttcagttt tttatctgca gggtgatcgt gtgctggcag ttgataccgt taatcgtccg   1140

gttgaattta accagagcaa acaaattatc accgatcgtc tgccggtgga accgaatctg   1200

ctgggagatg aaagcgtgcc gctgaaagaa attattgcag cagcaaaagc agaactgagc   1260

agcgcataa                                                           1269
```